(12) United States Patent
Griffin et al.

(10) Patent No.: US 6,204,045 B1
(45) Date of Patent: *Mar. 20, 2001

(54) VIRAL NUCLEOTIDE SEQUENCES

(75) Inventors: Annette Mary Griffin; Matthew McKinley Binns; Simon D. Scott; Louis J. N. Ross, all of Huntingdon (GB)

(73) Assignee: Merial, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/133,409

(22) Filed: Aug. 13, 1998

Related U.S. Application Data

(62) Division of application No. 08/125,039, filed on Sep. 22, 1993, now Pat. No. 5,906,821, which is a continuation of application No. 07/669,391, filed as application No. PCT/GB89/01075 on Sep. 13, 1989, now abandoned.

(30) Foreign Application Priority Data

Sep. 13, 1998 (GB) .................................................. 8821441

(51) Int. Cl.⁷ .............................. C12N 15/869; C12N 7/01
(52) U.S. Cl. ..................................... 435/235.1; 435/320.1
(58) Field of Search .............................. 435/235.1, 320.1; 424/229.1, 93.2, 93.6, 186.1, 191.1, 204.1, 205.1, 209.1, 215.1, 225.1, 232.1, 271.1

(56) References Cited

U.S. PATENT DOCUMENTS 5,906,821 * 5/1999 Griffin et al. ..................... 424/229.1

OTHER PUBLICATIONS

Cohen, Science, vol. 265, pp. 1371–1373, Sep. 2, 1994.*

Rabinovich et al., Science, vol. 265, p. 1401–1404, Sep. 2, 1994.*

Jaenicke, Proq. Biophys. Molec. Biol., vol. 49, pp. 117–237, 1987.*

* cited by examiner

*Primary Examiner*—David Guzo
(74) *Attorney, Agent, or Firm*—Larson & Taylor PLC

(57) ABSTRACT

Various genes of herpes virus of turkeys (HVT), Marek's disease virus (MDV) and infectious laryngotracheitis virus (ILTV) have been identified as non-essential regions (and candidates for insertion sites for foreign genes) and/or as antigen-encoding regions. The former include the HVT homologue of the HSV (herpes simplex virus) gC gene, the TX (thymidine kinase) region of MDV or ILTV, ORF3 of ILTV (as defined herein), the ribonucleotide reductase (large subunit) gene of ILTV, MDV or HVT and the ribonucleotide reductase (small subunit) gene of MDV. The antigen-encoding regions include the HVT homologues of the HSV gB, gC and gH genes, the ILTV homologue of HSV gB, ORF2 of ILTV, and the HVT homologue of the HSV-1 immediate early genes IE-175 and IE-68. Manipulation of these genes allows vaccines to be prepared comprising attenuated virus or virus carrying heterologous antigen-encoding sequences.

5 Claims, 67 Drawing Sheets

FIG 2A

```
TCGAGCTCGCCGGGATGTTTAGTCACGATAGACATCGGT
         10        20        30       40
TCGCCCAGCCGTCGAATACAGCATTATATTTAGTGTTG
         50        60        70       80
AAAATGTAGGGCTGCTTCCTCACTTAAAGGAGGAAATGGCT
         90       100       110      120
CGATTCATGTTTCATAGCAGTAGAAAAACAGATTGGACCG
        130       140       150      160
TCAGTAAGTTTAGAGGGTTTTATGACTTTAGCACTATAGA
        170       180       190      200
TAATGTAACTGCGGCCCATCGCATGGCTTGGAAATATATC
        210       220       230      240
AAAGAACTGATTTTTGCAACAGCTTTATTTCTCTGTAT
        250       260       270      280
TTAAATGTGGCGAATTGCACATCTGTCGTGCCGACAGTTT
        290       300       310      320
GCAGATCAACAGCAATGGAGACTATGTATGGAAAAATGGA
        330       340       350      360
```

FIG 2B

```
ATATATATAACATATGAAACCGAATATCCACTTATAATGA
370        380        390        400
TTCTGGGTCAGAATCAAGCACTTCAGAAACGCAAAATAT
        410        420        430        440
GACTGCAATTATTGATACAGATGTTTTTCGTTGCTTTAT
        450        460        470        480
TCTATTTTGCAGTATATGGCCCCCGTTACGGCAGATCAGG
        490        500        510        520
TGCGAGTAGAACAGATTACCAACAGCCACGCCCCATCTG
        530        540        550        560
ACCCGTCCAATATTCTGTGTCCCTGCATTTTATCTCACA
        570        580        590        600
                                        M  H
CAATTTATGAACAGCATCATTAAGATCATCTCACTATGCA
        610        620        630        640
 Y  F  R  N  C  I  F  F  L  I  V  I
CTATTTTAGGCGGAATTGCATTTTTTCCTTATAGTTATT
        650        660        670        680
```

FIG 2C

```
L  Y  Y  G  T  N  S  S  P  S  T  Q  N  V  T
CTATATGGTACGAACTCATCTCCGAGTACCCAAAAATGTGA
         690       700       710       720

S  R  E  V  V  S  S  V  Q  L  S  E  E
CATCAAGAGAAGTTGTTTCGAGGTCCAGTGTCTGAGGA
         730       740       750       760

E  S  T  F  Y  L  C  P  P  P  V  G  S
AGAGTCTACGTTTTATCTTTGTCCCCACCAGTGGGTTCA
         770       780       790       800

T  V  I  R  L  E  P  P  R  K  C  P  E  P
ACCGTGATCCGTCTAGAACCGCGGAAAATGTCCCGAAC
         810       820       830       840

R  K  A  T  E  W  G  E  G  I  A  I  L
CTAGAAAAGCCACCGAGTGGGGTGAAGGAATCGCGATATTA
         850       860       870       880
```

FIG 2D

```
      F  K  E  N  I  S  P  Y  K  F  K  V  T
    TTTAAAGAGAATATCAGTCCATATAAGTTAAAGTGACGC
    ||||||||||||||||||||||||||||||||||||||
    GAGAATATCAGTCCGTATAAATTCAAAGTAACAC
          890        900        910        920

L  Y  Y  K  N  I  I  Q  T  T  T  W  T  G
    TTTATTATAAAAATATCATTCAGACGACGACATGGACGG
    |||  ||||  |||||||  ||  ||  ||||||||||
    TTTACTATAAGAACGTTATACAAACTACGACGTGGACTG
          930        940        950        960

T  T  Y  R  Q  I  T  N  R  Y  T  D  R
    GGACGACATATAGACAGATCACTAATGATATACAGATAG
    ||||||  ||  ||||||||  |||  |||||||||||||
    GGACGACGTACAGAGACAGATAACTAACAGGTATACAGATAG
          970        980        990        1000
```

FIG 2E

```
         T  P  V  S  I  E  E  I  T  D  L  I  D
        GACGCCCGTTCCATTGAAGAGATCACGGATCTAATCGAC
        ||  ||  ||||  ||||  ||||||  ||||  ||||  ||
        AACACCCGTGTCTATCGACGAAATTACTGATTTGATAGAT
              1010        1020        1030        1040

G  K  G  R  C  S  S  K  A  R  Y  L  R  N
        GGCAAAGGAAGATGCTCATCTAAAGCAAGATACCTTAGAA
        ||  |||  ||  ||  ||  |||  |||  |  |||  ||
        GGTAAGGGGAAATGTTCATCCAAAGCCCGTATCTTCG
              1050        1060        1070        1080

N  V  Y  V  E  A  F  D  R  D  A  G  E
        ACAATGTATATGTTGAAGCGTTTGACAGGGATGCGGGAGAA
              1090        1100        1110        1120

K  Q  V  L  L  K  P  S  K  F  N  T  P
        AAACAAGTACTTCTAAAACCATCAAAATTCAACACGCCC
              1130        1140        1150        1160
```

FIG 2F

```
         E   S   R   A   W   H   T   T   N   E   T   Y   T   V
       GAATCTAGGGCATGGCACACGACTAATGAGACGTATACCG
       ||||||||||||| ||| ||||||| |||||| ||||
       GGCATGGCATACGACCAACGAGACGTACACCG
              1170        1180        1190        1200

——V——
         W   G   S   P   W   I   Y   R   T   G   T   S   V
       TGTGGGATCACCATGGATATCGAACGGGAACCTCCGT
       |||||||| ||||||||||||| |||| || |||||
       TGTGGGGATCTCCATGGGTATATAGAACGGGCACGTCCGT
              1210        1220        1230        1240

——A——
         N   C   I   V   E   E   M   D   A   R   S   V   F
       CAATGTATAGTAGAGAAATGGATCCCGCTCTGTGTTT
       ||| || |||||| ||||||| ||||||| || |||
       CAACTGCATAGTAGTAGAAGAGATGGATGCCAGATCAGCATTT
              1250        1260        1270        1280
```

FIG 2G

```
         ---T---
         P  Y  S  Y  F  A  M  A  N  G  D  I  A  N
         CCGTATTCATATTTGCAATGGCCAATGGCGACATCGCGA
         ||| || |||||| ||||||||||||| || |||||||
         CCATACACGTACTTTGCAATGGCCAATGGAGATATCGCAA
              1290        1300       1310       1320

---M---      ---T---T---D---
         I  S  P  F  Y  G  L  S  P  P  E  A  A
         ACATATCTCCATTTTATGGTCTATCCCCACCAGAGGCTGC
         |||| ||||||||| ||||  ||||||| |||| || |
         ACATGTCTCCATTTTATGAACAACTCCAACCGACGCGGC
              1330       1340       1350       1360

---S---        ---R---R---
         A  E  P  M  G  Y  P  Q  D  N  F  K  Q
         CGCAGAACCCATGGGATATCCCCAGATAATTTCAAACAA
         ||| |||||| ||||| ||||||  ||||| ||| |||
         CGGGAGCCCATGAGCTATCCGCAAGACCGATTCAGGCAA
              1370       1380      1390       1400
```

FIG 2H

```
      -F-----------------------------------T-----
         -------------P-----------
      L  D  S  Y  F  S  M  D  L  D  K  R  R  K
      CTAGATAGCTATTTTCAATGGATTGGACAAGCGTCGAA
      |||  ||||||||  |  ||||||||||  |||  ||||
      TTTGACAGCTATTTCCCCATGGATTTGGATACGGCCGAA
            1410       1420       1430       1440

A  S  L  P  V  K  R  N  F  L  I  T  S
      AAGCAAGCCTTCCAGTCAAGCGTAACTTTCTCATCACATC
      ||
      AA
            1450       1460       1470       1480

H  F  T  V  G  W  D  W  A  P  K  T  T
      ACACTTCACAGTTGGGTGGGACTGGGCTCCAAAAACTACT
            1490       1500       1510       1520

R  V  C  S  M  T  K  W  K  E  V  T  E  M
      CGTGTATGTTCAATGACTAAGTGGAAAGAGTGACTGAAA
            1530       1540       1550       1560

L  R  A  T  V  N  G  R  Y  R  F  M  A
      TGTTGCGTGCAACAGTTAATGGAGATACAGATTTATGGC
            1570       1580       1590       1600
```

FIG 2I

R  E  L  S  A  T  F  I  S  N  T  T  E
CCGTGAACTTCGGCAACGTTTATCAGTAATACGACTGAG
      1610      1620      1630      1640

F  D  P  N  R  I  I  L  G  Q  C  I  K  R
TTTGATCCAAATCGGCATCATATTAGGACAATGTATTAAAC
      1650      1660      1670      1680

E  A  E  A  A  I  E  Q  I  F  R  T  K
GCGAGGCAGAAGCAGCAATCGAGCAGATATTTAGGACAAA
      1690      1700      1710      1720

Y  N  D  S  H  V  K  V  G  H  V  Q  Y
ATATAATGACAGTCACGTCAAGTTGGACATGTACAATA
      1730      1740      1750      1760

F  L  A  L  G  G  F  I  V  A  Y  Q  P  V
TTTCTTGGCTCTCGGGGATTTATTGTAGCATATCAGCCTG
      1770      1780      1790      1800

L  S  K  S  L  A  H  M  Y  L  R  E  L
TTCTATCCAAATCCCTGCTCATATGTACCTCAGAGAATT
      1810      1820      1830      1840

FIG 2J

```
      M  R  D  N  R  T  D  E  M  L  D  L  V
      GATGAGAGACAACAGGACCGATGAGATGCTGACCTGTA
              1850      1860      1870      1880

N  N  K  H  A  I  Y  K  K  N  A  T  S  L
      AACAATAAGCATGCAATTTATAAGAAAAATGCTACCTCAT
              1890      1900      1910      1920

S  R  L  R  R  D  I  R  N  A  P  N  R
      TGTCACGATTGCGGCGAGATATTCGAAATGCACCAAATAG
              1930      1940      1950      1960

K  I  T  L  D  D  T  T  A  I  K  S  T
      AAAAATAACATTAGACGACACCACAGCTATTAAATCGACA
              1970      1980      1990      2000

S  S  V  Q  F  A  M  L  Q  F  L  Y  D  H
      TCGTCTGTTCAATTCGCCATGCTCCAATTTCTTATGATC
              2010      2020      2030      2040

I  Q  T  H  I  N  D  M  F  S  R  I  A
      ATATACAAACCCATATATTAAATGATAGTTTAGTAGGATTGC
              2050      2060      2070      2080
```

FIG 2K

```
       T  A  W  C  E  L  Q  N  R  E  L  V  L
      CACAGCTTGGTGCCGAATTGCAGAATAGAGAACTTGTTTA
              2090        2100        2110        2120

W  H  E  G  I  K  I  N  P  S  A  T  A  S
      TGGCACGAAGGGATAAAGATTAATCCTAGCGCTACAGCGA
              2130        2140        2150        2160

A  T  L  G  R  R  V  A  A  K  M  L  G
      GTGCAACATTAGGAAGGAGAGTGGCTGCAAAGATGTTGGG
                                       GCCAAAATGTTGGG
              2170        2180        2190        2200
                                       I--E--T---S--
      ---D--------                     
       D  V  A  A  V  S  S  C  T  A  I  D  A
      GGATGTCGCTGCTGTATCGAGCTGCACTGCTATAGATGCG
      TGACGATGCCGCCGTATCATCATGTATTGAGACTGATTCA
              2210        2220        2230        2240
```

FIG 2L

```
         -D-                                          -V-
          E  S  V  T  L  Q  N  S  M  R  V  I  T  S
         GAATCCGTCACTTTGCAAATTCTATGCGAGTTATCACAT
         ||||||||||||| || ||||||||| |||||||||||
         GATTCTGTTACCTTACAAATTCCATGCGGGTTGTCACCT
              2250      2260      2270      2280

T  N  T  C  Y  S  R  P  L  V  L  F  S
         CCACTAATACATGTTATAGCCGACCATTGTTCTATTTC
         ||  |||||| || |||||||| |||||| || |||
         CTACCAATACTGTTATAGCCGGCCCTTTAGTGTTATTCTC
              2290      2300      2310      2320

---D---R---D---K-
          Y  G  E  N  Q  G  N  I  Q  G  Q  L  G
         ATATGGAGAAACCAAGGAAACATACAGGACAACTCGGTG
         ||||  ||||| ||||| ||||||| |||||||| |||
         CTACGGGGACCGACAAGACAAATACAAGACAGTTGGGGG
              2330      2340      2350      2360
```

FIG 2M

```
        E   N   E   L   L   P   T   L   E   A   V   E   P
     AAAACAACGAGTTGCTTCCAACGCTAGAGGCTGTAGAGC
     |||||| ||  ||| |||||| ||||||| |||||| |||||
     AAAACAATGAATTGATTCCAACTCTAGAGGCCATAGAGC
           2370         2380         2390      2400

C   S   A   N   H   R   R   Y   F   L   F   G   S
     CATGCTCGGCTAATCATCGTAGATATTTCTGTTTGGATC
     |||| |||| ||||| |||||||| |||||||||||||
     CATGTTCGGCCAATCATCGTAGA
           2410         2420         2430      2440

G   Y   A   L   F   E   N   Y   N   F   V   K   M
     CGGTTATGCTTTATTTGAAAACTATAATTTGTTAAGATGG
           2450         2460         2470      2480

V   D   A   A   D   I   Q   I   A   S   T   F   V   E
     TAGACGCTGCCGATATACAGATTGCTAGCACATTGTCG
           2490         2500         2510      2520
```

FIG 2N

```
  L  N  L  T  L  L  E  D  R  E  I  L  P
AGCTTAATCTAACCCTGCTAGAAGATCGGGAAATTTGCC
        2530      2540      2550      2560

L  S  V  Y  T  K  E  E  L  R  D  V  G
TTTATCCGTTTACACAAAAGAGAGTTGCGTGATGTTGGT
        2570      2580      2590      2600

V  L  D  Y  A  E  V  A  R  R  N  Q  L  H
GTATTGGATTATGCAGAAGTAGCTCGCCGCAATCAACTAC
        2610      2620      2630      2640

E  L  K  F  Y  D  I  N  K  V  I  E  V
ATGAACTTAAATTTTATGACATAAACAAAGTAATAGAAGT
        2650      2660      2670      2680

D  T  N  Y  A  F  M  N  G  L  A  E  L
GGATACAAATTACGCGTTTATGAACGGTTTGGCCGAATTG
        2690      2700      2710      2720

F  N  G  M  G  Q  V  G  Q  A  I  G  K  V
TTTAACGGTATGGGTCAGTAGGCAAGCTATAGGCAAAG
        2730      2740      2750      2760
```

FIG 2ρ

```
  V   V   G   A   A   G   A   I   V   S   T   I   S
TTGTAGTAGGGGCTGCCGGTGCAATCGTATCTACCATATC
    2770        2780        2790        2800

G   V   S   A   F   M   S   I   P   L   G   L   S
TGGTGTCTCTGCTTTCATGTCAATCCCTTTGGGCTTTCG
    2810        2820        2830        2840

A   I   G   L   I   I   I   A   G   L   V   A   A   F
GCAATCGGTTTAATCATTATAGCAGGACTCGTGGCTGCAT
    2850        2860        2870        2880

L   A   Y   R   Y   V   N   K   L   K   S   N   P
TTTTAGCATATCGTTATGTAAACAAGCTTAAAAGCAATCC
    2890        2900        2910        2920

M   K   A   L   Y   P   M   T   T   E   V   L   K
AATGAAAGCCCTTTATCCTATGACAACAGAAGTGCTTAAG
    2930        2940        2950        2960

A   Q   A   T   R   E   L   H   G   E   E   S   D   D
GCACAGGCAACGCGTGAGTTGCATGGCGAGGAATCAGATG
    2970        2980        2990        3000
```

FIG 2P

```
  L   E   R   T   S   I   D   E   R   K   L   E   E
ATTTGGAACGAACATCTATTGATGAAAGAAAATTAGAAGA
        3010        3020        3030        3040

A   R   E   M   I   K   Y   M   A   L   V   S   A
AGCTAGAGAAATGATAAAATATATGGCGTTAGTCTCCGCG
        3050        3060        3070        3080

E   E   R   H   E   K   K   L   R   R   K   R   R   G
GAAGAACGCCACGAGAAAAACTGCGGAGAAAGAGGCGAG
        3090        3100        3110        3120

T   T   A   V   L   S   D   H   L   A   K   M   R
GCACTACCGCCGTTCTATCGGACCACCTGGCAAAAATGAG
        3130        3140        3150        3160

I   K   N   S   N   P   K   Y   D   K   L   P   T
GATTAAAAAATAGTAACCCTAAATATGATAAGTTACCTACT
        3170        3180        3190        3200

T   Y   S   D   S   E   D   D   D   A   V   *
ACATATTCAGACTCAGAAGATGATGCTGTGTAAGTGGGCA
        3210        3220        3230        3240

CTATTTATATTGAACTGAATAAAAACGCATAGAGCATGATA
        3250        3260        3270        3280
```

FIG 2Q

```
TGGTTTACTCATTATTGGAGATATAAAGCATATTCAAT
     3290           3300           3310           3320
ACGATATATTGCGAACGTGATGCTAAAAACATAGCTCCCT
     3330           3340           3350           3360
GTATTATTGATGCGCCATCATTTGATTAATAAATACATCG
     3370           3380           3390           3400
ACGCCGGCATCACTGGTGCGGTGTATACCAGCTACGGCGC
     3410           3420           3430           3440
TAGCCATTCATGGTATCCCGTGATTGCTCGATGCTTTCCTT
     3450           3460           3470           3480
CTGAATTCCGTCGGAACGCTCCTGAGAGATGGTGCAGTT
     3490           3500           3510           3520
ATTGGTACATTTCGACCAGCCTCCGATCTGAAACTGGCA
     3530           3540           3550           3560
CAGGAATGCACCGTGGAATTGGTAGAAGTTTTTCCTTCCG
     3570           3580           3590           3600
```

FIG 2R

TGGAAGGCATAGGGCGTTCGACTCCCATGGGCCATGAAACTGTGGGATGT
3610      3620      3630      3640      3650

FIG. 4A

```
TATTATTGGTCCATGCTAGAATAGTCATACGCTACGATCT
         10        20        30        40
GTTGCTATATATGACTATCGCCAAACTGTTAAACCCGCGA
         50        60        70        80
AGAATATATTTCATATAAACCTAAGGGCCCCTCAGTCTGA
         90       100       110       120
                       M   K   F   Y   C   L
TTTTTTGTGAAAACGTGTATACCATGAAGTTTTACTGCCT
        130       140       150       160
  I   R   F   M   I   I   A   N   L   Y   S   S   Y
AATCCGTTTCATGATCATAGCGAATCTTTATTCATCTTAC
        170       180       190       200
  Q   I   S   L   P   G   T   Y   P   S   Q   I   L   L
CAAATATCGCTTCCAGGCACATATCCATCGCAAATATTGC
        210       220       230       240
  D   M   K   N   S   P   L   V   R   F   N   I   S
TTGACATGAAGAACTCGCCGCTCGTACGCTTTAATATATC
        250       260       270       280
```

FIG 4B

```
         T   R   D   Y   K   D   E   T   L   W   I   R   K
        GACGCGTGATTATAAAGAGACGAGAGACACTCTGGATACGGAAA
             290          300          310          320

N   S   T   F   V   Y   I   D   T   A   V   T   T   A
    AATTCGACATTTGTTTATATCGATACGGCTGTGACGACAG
         330          340          350          360

N   V   I   F'  Y   L   P   I   G   Q   V   R   Q
    CGAACGTTATCTTTTATCTGCCGATCGGTCAGGTACGACA
         370          380          390          400

M   V   F   F   K   R   P   I   S   R   L   L   T
    AATGGTTTTTTTCAAGCCGTCCAATATCCAGGCTACTAACG
         410          420          430          440

S   N   N   L   V   K   F   I   N   T   G   S   Y   A
    TCCAATAACCTGGTTAAATTTATTAATACCGGTTCATACG
         450          460          470          480

N   H   T   F   K   T   E   L   S   P   Y   L   S
    CCAATCATACATTCAAGACAGAACTTTCACCCTATTTGTC
         490          500          510          520
```

FIG 4C

```
  K   T   N   T   P   L   K   K   Y   E   I   V   V
GAAAACCAATACACCGTTGAAGAAATATGAAATTGTTGTC
         530           540          550         560

D   Q   P   T   G   E   N   P   P   A   G   F   G   S
GATCAACCTACTGGAGAAAACCCTCCGGCAGGGTTCGGAA
         570          580           590         600

L   K   P   A   D   F   L   N   P   G   Y   K   F
GTTAAAACCGGCAGACTTTCTCAACCCCGGATACAAGTT
         610          620           630         640

V   L   T   S   E   L   V   G   A   Y   T   K   R
CGTTCTCACAAGCGAGTTGGTAGGAGCCTACACAAAACGA
         650          660          670          680

S   C   F   V   D   P   M   D   S   L   V   P   I   D
TCTTGTTTTGTCGATCCGATGGATTCTCTCGTCCCGATAG
         690          700          710          720

Y   D   H   V   R   T   I   I   F   G   S   A   G
ATTATGATCATGTACGAACCATTATATTCGGATCTGCTGG
         730          740          750          760
```

FIG 4D

```
      M   E   I   L   M   K   M   G   I   T   L   A   S
GATGGAGATTTTAATGAAGATGGGAATTACTTTGGCATCT
            770         780         790         800

M   T   I   S   T   K   Y   N   P   P   I   E   L   I
ATGACCATTTCGACGAAATATAATCCTCCTATTGAACTGA
            810         820         830         840

I   S   A   K   Y   R   N   L   S   L   L   W   P
TAATATCTGCAAAGTACCGAAATTTATCACTGTTGTGGCC
            850         860         870         880

P   R   Q   Q   Y   E   P   V   N   K   G   T   G
ACCCCGACAACAATATGAACCTGTAAATAAAGGGACTGGA
            890         900         910         920

R   P   H   W   I   Y   L   L   G   V   Y   R   N   V
CGCCCCATTGGATCTACCTATTAGGTGTGTATAGAAACG
            930         940         950         960

S   D   S   E   R   D   S   Y   M   N   M   I   K
TTTCGGACTCCGAGCGTGACTCATACATGAATATGATTAA
            970         980         990         1000
```

FIG 4E

```
  S   L   G   D   S   M   D   Y   H   F   L   I   S
GAGTCTGGGCGATTCTATGGATTATCACTTCCTAATTAGC
                1010        1020        1030        1040

R   A   H   A   Q   M   L   I   L   L   A   A   E   D   R
AGAGGCGCATGCCCAGATGCTGATACTGGCAGCAGAGGACC
                1050        1060        1070        1080

L   V   D   E   M   H   S   F   R   N   V   I   A
GGCTCGTGGATGAAATGCATAGTTTCAGGAACGTTATTGC
                1090        1100        1110        1120

R   L   F   V   S   L   F   A   F   I   R   N   A
GCGTTTATTTGTATCGTTGTTCGCATTCATACGTAACGCA
                1130        1140        1150        1160

F   Q   S   G   Y   T   S   L   N   D   I   E   I
TTTCAGTCTGGCTACACCTCTCTTAATGACATAATTGAAA
                1170        1180        1190        1200

E   A   D   L   R   L   I   V   E   G   I   S   S
TCGAAGCCGATTTGAGGTTAATTGTAGAAGGCATTTCTTC
                1210        1220        1230        1240
```

FIG 4F

```
    A   A   F   R   K   D   A   S   T   H   F   L   L   I
TGCTGCATTTCGTAAAGACGCTAGTACACACTTTCTTATA
         1250        1260        1270        1280

S   G   T   P   I   K   D   S   K   A   D   L   I   K
TCGGGAACGCCCATAAAAGATAGCAAAGCGGATTAATTA
         1290        1300        1310        1320

S   L   L   S   K   V   I   R   P   I   S   G   H
AATCGTTGTTGTCTAAAGTCATTCGACCAATTTCCGGACA
         1330        1340        1350        1360

T   R   P   L   S   A   I   Q   H   L   F   L   L
TACACGTCCCTTATCTGCGATACAACATCTATTCCTTTTG
         1370        1380        1390        1400

R   S   A   Y   A   L   D   I   P   R   Q   N   G   S
AGATCCGCTTATGCATTGGATATACCCCGTCAAAACGGAT
         1410        1420        1430        1440

L   S   E   Q   V   S   T   V   A   L   S   F   I
CTTTGAGCGAACAGGTATCTACAGTGGCACTGTCGTTCAT
         1450        1460        1470        1480
```

FIG 4G

```
  E  N  I  H  S  E  A  M  R  D  I  L  S
TGAAAATATTCACAGGCGAGGCCATGAGGGACATTCTGTCA
         1490      1500      1510      1520

W  N  T  T  K  H  A  L  Y  Y  A  F  A
TGGAACACTACAAAGCATGGCGTTGTATTATGCATTCG
         1530      1540      1550      1560

S  I  L  Q  R  P  L  T  E  W  G  A  S
CGAGTATTTTGCAACGGCCACTGACCGAATGGGGCGCCCTC
         1570      1580      1590      1600

R  N  A  R  R  A  I  L  L  A  S  S  M
AAGAAATGCACGGAGGGCAATACTATTAGCATCATCGATG
         1610      1620      1630      1640

C  T  E  E  H  V  I  A  T  E  L  A  I  Q
TGTACAGAAGAGCATGTTATCGCAACTGAGTTGGCTATTC
         1650      1660      1670      1680

E  L  Y  V  K  I  R  S  N  A  D  P  I
AAGAACTGTATGTCAAAATCAGAAGTAATGCCGACCCAAT
         1690      1700      1710      1720
```

FIG 4H

```
         H  L  L  D  V  Y  T  P  C  L  S  S  L
       ACACCTTCTAGACGTATATACACCATGTCTTTCTTCACTA
              1730          1740         1750       1760

R  L  D  L  S  E  H  H  R  I  Y  A  M  A
       CGATTGGACCTTTCCGAACACCATCGGATATACGGCAATGG
            1770         1780         1790       1800

D  V  V  F  Y  P  D  I  Q  Q  Y  L  K
       CAGATGTAGTTTTCTATCCAGACATTCAGCAGTATTTGAA
           1810         1820        1830        1840

K  K  S  H  E  G  N  M  K  E  D  D  L
       AAAAAAATCCCATGAGGGTAATATGAAGGAAGATGATCTC
           1850         1860         1870        1880

E  T  K  A  E  Y  I  L  T  K  L
       GAAACAAAGGCGGAATACATCCTCACCAAGCTT
           1890         1900         1910
```

FIG 5A

```
AAGCTTTTTGTAAAAACGATTATGACCACGGACACCCGCT
         10         20        30        40

TTTAGCAATCCTGCCATAAGGTGGTTTCCCGCGTGCTTGC
         50        60         70        80

CTCGAAGACAATGCCAGCTAATCCAGCCATTACCATATTT
         90        100        110       120

|——S——Q——
                              M   A   L   P
                              |||||| ||
                              ATGGCATCTCA
CCTTGGCTTGCATTTGGATCTGCCGTCGATGGCATTGCC
         130        140       150       160

—M——T——S——A——Q——I——
  R   R   P   P   T   L   T   R   V   Y   L   D   D   G
GAGAGACCGCCCACGTTAACGCGAGTTTATCTAGACGGA
 ||  ||  ||  || || ||  ||  ||  ||  ||  ||  ||  ||
GATGACATCTGCACAGTCATACGTGTATACCTCGATGA
         170        180       190        200
```

FIG 5B

```
 -S--M----------------M------E--I--
  P  F  G  I  G  K  T  S  I  L  N  A  M  P
 CCGTTTGGTATAGGCAAAACGTCTATACTAAACGCTATGC
  |  ||||||  ||||||||  |||||||  ||  |||
 TCAATGGGTATAGGTAAAACGTCAATGTTGAATGAGATAC
         210       220       230       240

----T----L|
  D  H  T  P  D  G  A  P  I  L  K  V  Y
 CCGACCACACGCCCCGATGGGGCTCCTATATTGAAAGTGTA
     ||
 CGACGCATCTT
         250       260       270       280

E  P  M  K  Y  W  R  C  Q  S  T  D  L
 CGAACCAATGAAATATTGGAGATGCCAGTCTACCGATTTG
         290       300       310       320
```

FIG 5C

```
          |————————R————————|
      V V A A A N E T P E R R R R G G
      GTGGTAGCTGCCAACGAAACGCCAGAACGTAGGCGTGGTG
                                  ||| || || |||
                                  ATCGTCGTCGCAGGG
      330       340       350       360

|——E——F——|  |——L——|         |——S——|         |——V——T——A——|
  A L S G F Q S D M I M A S
  GAGCTTTATCACGATTCCAATCTGACATGATCATGGCATC
  ||| ||  |||| ||||| |||| ||||| |||||  ||
  GAGAGTTTTCTTTATTCAATCTAGCATGATTGTAACAGC
      370       380       390       400

|——L——|  |——S——K——|                      |——V——|
  I Q A R F A D P Y L L F H
  TATACAAGCCAGATTTGCCGATCCATATTGCTTTTCAC
  || ||||| ||||| |||| |||||||| ||  |||
  TTTACAATCAAAGTTTGCAGATCCCTATCTTGTATTTCAT
      410       420       430       440
```

FIG 5D

```
                    H—R—I—T—G—T—R
                    H   R  I  T  G  T  R
ERLSSKCRGKIEIC
E R L S S K C R G K I E I C
GAACGGTTATCATCTAAATGTAGAGGAAAATAGAAATAT
|| ||||| ||  ||| ||   | |||||||| |||||
GAGGCGCTTATCGTCGAAGTGTCATCGCATAACAGGAACAC
        450       460       470       480

——G—N——S—L——I—
  D T P A I I L M L D R H P
  D   T   P   A   I   I   L   M   L   D   R   H   P
GCGATACTCCAGCAATTATATGCTGGATAGGCACCC
|| ||| || ||||||||||||||  ||||   |||
GTGGCAATCCATCGCTTATATTAATTCTAGATGACATCC
        490       500       510       520

——I—S——T—V——A——H—
  V A A I L C F P I T R Y L
  V   A   A   I   L   C   F   P   I   T   R   Y   L
TGTGGGCGGATATTATGTTTCCCAATCACTCGCTATTA
|| ||| || |||||||||||| || || ||||||||
CATATCCGCTACCGTATGTTTCCCATTGCTCGACATTA
        530       540       550       560

FIG 5E

```
 -T----D--C-----------------------------------------M--------
  L  G  E  Y  S  L  E  M  L  I  S  S  I
 CTTGGAGAATATCTTTGAAATGTTGATTAGCTCTATAA
 ||||  |||||||  |||  ||| ||||| ||||  ||
 ACTGGAGAGATTGTTCCTTGAGATGCTAATTAGTATGATAA
        570         580        590        600

----------Q-------------P--------------V--I------
  R  L  P  L  E  S  P  G  C  N  L  T  V
 TAAGACTTCCGTTGGAATCCCCGGATGCAACCTGACAGT
 |||   |||   ||| |||||| ||||||||  || |
 TAAGGTTGCCCCAGGAACCGCCAGGATGCAACTTGTGAT
            610         620        630         640

--V--D----------H-------------------S----L--
  T  I  L  P  D  E  K  E  H  V  N  R  I
 CACAATCCTTCCCGACGAAAGGAACACGTTAATAGGATT
 |||   |||||||||||||||||||  |||| ||||||
 TGTCGATCTACATGACGAAAGGAGCATGTTAGCCGTCTA
           650         660        670         680
```

FIG 5F

```
  S        N        T        K        T        L    L
  C    S   R   D   R   P   G   E   T   A   D   R   N   M
TGTTCAAGAGATAGACCGGGTGAAACGGCAGATAGAAATA
||||  ||||   |||   ||   ||   ||||   ||||
TCTTCACGGAATAGGACCGGCGAGAAACAGATCTACTAA
          690            700            710            720

A                    S   C
  L   R   T   L   N   A   V   Y   A   S   L   V   D
TGCTCAGAACACTCAATGCCGTATACGCCATCTTTGGTGGA
|||   ||||   ||||   ||||||||   ||   ||   ||
TGCTCAGGGCACTTAAATGCAGTGTATTCCTGTTTAGTAGA
          730            740            750            760

I    M        H    I        S
  T   V   K   Y   A   N   L   T   C   P   Y   E   K
CACGGTTAAATACGCAAATCTAACATGCCCTTACGAGAAA
|||   |||   ||||||||||   ||   ||||   ||
CACTATTATGTACGCAAATCATATTTGTCCCTACAGTAAG
          770            780            790            800
```

FIG 5G

```
-D--E------S------D------------D
 E  S  W  E  M  E  W  L  G  L  P  W  F  E
GAAGCTGGGAAATGGAATGGAATGGTTGGACTTCCCTGTTTG
 ||||||  |||||||||||  ||  ||  |||||||||||
GATGAATGGGAATCTGAATGGTTGGATCTACCATGGTTTG
         810        820        830        840

-------T----A--T--T------N---E----------T
 E  S  L  L  E  E  F  I  S  R  P  R  P
AAGAGTCATTACTTGAAGAATTCATCTCCGCCCCGCCC
 ||  ||  ||  ||  ||  ||  ||  ||  ||  ||
ATACATCTTTGCCCACAACGTTTATAAACGAACCTCGTAC
         850        860        870        880

----D--Y--R--G--S------V--S------H---H-------
 V  I  C  S  R  T  R  M  P  L  D  R  T
TGTTATTGTTCGAGAACTCGAATGCCGCTGACCGAACT
 ||  ||  ||  ||  ||  ||  ||  ||  ||  ||
TG...ATTATGCGGTAGTAGGGTGTCATTACACCATACG
         890        900        910        920
```

FIG 5H

```
              |————————R————————|
   L  L  A  I  F  K  R  R  K  E  L  C  S  E  N
   CTCCTGGCCATTTTTAAACGGAAAGAGCTGTGTAGCGAAA
   ||| | ||| |||||||   |||  ||   |
   CTTTTAGGATATATTTAAGCGGGCGAGAATTATGT
         930       940       950       960

G  E  L  L  T  Q  Y  S  W  I  L  W  G
   ATGGGGAGCTGTTAACTCAGTATTCTTGGATATTGTGGGG
         970       980       990       1000

L  L  T  K  L  H  T  I  N  V  E  L  F
   ATTACTGACTAAACTACACACCATTAAATGTCGAATTATTT
         1010      1020      1030      1040

|————V——E——L——L
   D  I  S  G  M  S  R  R  E  C  A  S  A  I
   GACATTAGCGGTATGTCACGTCGAGAATGCGCCAGGCTA
                                    ||  ||
                                    TGTGTAGAACTGC
         1050      1060      1070      1080
```

FIG 51

```
         D          S             V     H   S
         M H T M P E R L S T L A S
     TAATGCATACTATGCCGAGAGATTGTCTACTCTCGCTAG
     |||  ||||||||||||||| ||||||||| |||
     TTATGGATACTATGTCGAGAGATTGTAACACATAGTAG
        1090       1100       1110      1120

A  F      I        A      L   A
         W N D L C E L E D D V I S
     CTGGAATGATTTATGCCAGCTTGAAGATGATGTAATTTCC
     ||||||||||| |||  ||||||||| |||||
     CTGGAATGATGCCTTCGAGATTGAAGCTGATGTACTAGCC
        1130       1140       1150      1160

E     A  M   *
         Y N K G M C N E V G A S R *
     TATAATAACGGAATGTGTAACGAGGTTGGAGCGTCTCGAT
     ||||||||| ||||  ||||  ||||||
     TATAATAAAGAGATGGCTATGTAA
        1170       1180       1190      1200

AATTCTTCTTAATCTGCTGGTATTGGTTACTGCCATAACT
        1210       1220       1230      1240
```

FIG 5J

TATTATTGGTCCATGCTAGAATAGTCATACGCTACGATCT
     1250                1260           1270           1280

GTTGCTATATATGACTATCGCCAAACTGTTAAACCCGCGA
     1290                1300           1310           1320

AGAATATATTTCATATAAACCTAAGGGCCCCTCAGTCTGA
     1330                1340           1350           1360

TTTTTTGTGAAAAACGTGTATACCA
     1370                1380

FIG 6A

1 CAGCTGCCTAGTGAGTGAAATCTATACTGGGATTT
ATCATAACTAGTTTACTTGTTGTATATTAGTAGCGCTATCT
TGACCAAATCGTTGTTCACATCTTGGCCATATACGTATTGATC

121 GTTGTTTCGAACCGCGAATAAAACTTTCATACATAC
TAAACGATGGAGTTGTGTTTATGAGCGTTGAAAACAAAGT
ACCATCGGTTTAAAACTAAGTTGCATATCGTAATCCACAAAA

241 ATCATTTTATACATCATCCCGAAGAGACACCAAACG
                    M  L  T  P  R  V
TAACCCTCTACATATCTTCCCTCATGCTCACGCCGCGTGTGT
T  Y  E  S  F  V  D  *  (see below)
L  R  A  L  G  W  T  G  L  F  F  F  L  L  L  S
TACGAGCTTTGGGGTGGACTGGACTCTTTTTTTGCTTTTAT P  S  N  V  L  G  A  S  L  S  R
361 CTCCGAGCAAGTCCTAGGAGCCAGCCTTAGCCGG
D  L  E  T  P  P  F  L  S  F  D  P  S
GATCTCGAAACACCCCCATTTCTATCCTTTGATCCATCCA

FIG 6B

```
      N  I  S  I  N  G  A  P  L  T  E  V  P  H  A  P
    ACATTTCAATTAACGGCGGCCCTTAACTGAGGTACCTCATGCAC
                  S  T  E  S  V  S  T  N  S  E  S  T
481 CTTCCACAGAAGTGTCAACAAATTCGAAAGTACC

N  E  H  T  I  T  E  T  T  G  K  N  A  Y
    AATGAACATACCATAACAGAAACGACGGCAAGAACGCATACA
      I  H  N  N  A  S  T  D  K  Q  N  A  N  D
    TCCACAACAATGCGTCTACGGACAAGCAAAATGCGAACG
                  T  H  K  T  P  N  I  L  C  D  T  E
601 ACACTCATAAACGCCCAATATACTCTGCGATACGGA

E  V  F  V  F  L  N  E  T  G  R  F  V  C
    AGAAGTTTTGTTTTCCTTAACGAAACGGGAAGATTTGTTTGT
      T  L  K  V  D  P  P  S  D  S  E  W  S  N
    ACTCTCAAAGTCGACCCCCCTCGGATAGTGAATGGTCCA
                  F  V  L  D  L  I  F  N  P  I  E  Y
721 ACTTTGTTCTAGATCTTGATCTTTAACCAATTGAATA

H  A  N  E  K  N  V  E  A  A  R  I  A  G
    CCACGCCAACGAAAGAATGTGGAAGCGGCGCGTATCGCTGGT
```

FIG 6C

```
      L  Y  G  V  P  G  S  D  Y  A  Y  P  R  Q
     CTCTATGGAGTCCCCGGATCAGACTATGCATACCCAGTC

S  E  L  I  S  S  I  R  R  D  P
841  AATCTGAATTAATTTCTTCGATTCGACGAGATCCCC

Q  G  T  F  W  T  S  P  S  P  H  G  N  K
     AGGGCACATTTGGACGAGCCCATCACCTCATGAAACAA

Y  F  I  W  I  N  K  T  T  N  T  M  G  V  E
     GTACTTCATATGGATAAACAACAACCAATACGATGGGCGTGG

I  R  N  V  D  Y  A  D  N  G  Y
961  AAATTAGAAATGTAGATTATGCTGATAATGGCTAC

M  Q  V  I  M  R  D  H  F  N  R  P  L
     ATGCAAGTCATTATGCGTGACCATTTAATCGGCCTTAA
      I  D  K  H  I  Y  I  R  V  C  Q  R  P  A  S  V
     TAGATAAACATATTTACATACGTGTGTCAACGACCTGCATCAG

D  V  L  A  P  P  V  L  S  G  E  N
1081 TGGATGTACTGGCCCCTCCAGTCCTCAGCGGAGAAAA

Y  K  A  S  C  I  V  R  H  F  Y  P  P  G
     TTACAAGGCATCTGTATCGTTAGACACTTTTATCCCCCTGGA
```

FIG 6D

```
         S V Y V S W R Q N G N I A T
     TCTGTCTATGTATCTTGGAGACAGAATGAAACATTGCAA

P R K D R D G S F W W F
1201 CTCCTCGAAAGATCGCGATGGAAGTTTTGGTGTT

E S G R G A T L V S T I T L
     CGAATCTGGTAGAGGAGCTACGTTGTTTCTACAATAACATTG

G N S G I D F P P K I S C L
     GGAAATTCAGGAATTGATTCCCCCCAAAATATCTTGTC

V A W K Q G D M I S T T
1321 TGGTTGCCTGGAAGCAGGGTGATATGATCAGCACGAC

N A T A I P T V Y H H P R L
     GAATGCCACAGCTATCCCGACGGTATATCATCATCCCCGTTA

S L A F K D G Y A I C T I E
     TCCCTGGCTTTTAAAGATGGTTATGCAATATGTACTATAG

C V P S E I T V R W L V
1441 AATGTGTCCCCTCTGAGATTACGTACGTGGTTAGT

H D E A Q P N T T Y N T V V
     ACATGATGAAGCGCAGCCTAACACAACTTATAATACTGTGTT
```

FIG 6E

```
       T  G  L  C  R  T  I  D  R  H  R  N  L  L
      ACAGGTCTCTGCGCCATCGATCGCCATAGAAATCTCC
                            S  R  I  P  V  W  D  N  W  T  K  T
1561 TCAGCCGCATTCCAGTATGGGACAATTGGACGAAAAC
       K  Y  T  C  R  L  I  G  Y  P  F  D  E  D
      AAAATATACGTGCAGACTCATAGGCTACCCCTTCGATGAAGAT
       K  F  Q  D  S  E  Y  Y  D  A  T  P  S  A
      AAATTCAAGATTCGGAATATTACGATGCAACTCCATCTG
                            R  G  T  P  M  V  I  T  V  T  A  V
1681 CAAGAGAACACCCATGGTTATTACGGTTACGGCAGT
       L  G  L  A  V  I  L  G  M  G  I  I  M  T
      TTTGGGATTGGCTGTAATTTTAGGGATGGGGATAATCATGACT
       A  L  C  L  Y  N  S  T  R  K  N  I  R  L
      GCCCTATGTTTATACAACTCCACGAAAAAATATTCGAT
                            *
1801 TATAAATCTCATTGTTATGTAGTTGTGATTTATTAAAC
      ATATTTTTTATAACTCTAGTATTCTCCGAGTACTTATATATT
```

FIG 6F

TATTTGTCAGACAATAATGCAATAGTGGAGAAACGTGAGG

1921 GGAGTCTCTGTAAACAGAATACGTATAATCATCTATTTG

AATAAAAGATTGTGGTATAAATGAAGATAGCGCAAGTCATTC

CAAGCTCTCCATTCTATTTAAACAATGTACAGTTAAAGT

FIG 7A

```
  1 GAATTCTTGTAAAATATCATTAATTCCGCTACCAACGGGTTCCTTTTTTCACATAGCTG
    F  E  Q  L  I  D  N  I  G  S  G  V  P  E  K  K  E  C  L  Q

61 CTGCTCCCGTAGTTATCTTTTTTGCTGGAACCATTTCCCCAGGAAGTACGGGTCATTCTC
    Q  E  T  T  I  K  K  A  P  V  M  E  G  P  F  Y  P  D  N  E

121 AGAAATGGTCCTAGCGGATCTCTTCCGAGGGTTATTCTCCGAGTATTCGCTATCCCGTTT
    S  I  T  R  A  S  R  K  R  P  N  N  E  S  Y  E  S  D  R  K

181 ATTATTTTCTCAAGAGCCGAAATCAAGGCATCTAAGCGTGAAACAACAGTCTGCTCATG
    N  N  K  E  L  A  S  I  L  A  D  L  R  S  V  V  T  Q  E  H

241 TAATGATGGATACTGTATAGGATACGTTCCAGCCCCAGGAAACTGGCCGAAGTTCGAACT
    L  S  P  Y  Q  I  P  Y  T  G  A  G  P  F  Q  G  F  N  S  S

301 ATAATAAATTTGGATGCACGGGGTAAGTAGATGCGCTTTGATAAGGAATATATGGGAA
    Y  Y  N  P  H  V  P  Y  T  S  A  P  S  Q  Y  P  I  Y  P  F

361 ACGCCCGCAGAAATTTGGGTCTTCGTAAAGAGCCGGTCTGTAAGTGTGGTTCATCCCCGG
    R  G  C  F  N  P  D  E  Y  L  A  P  R  Y  T  H  N  M  G  P
```

FIG 7B

```
421 ACCCATAAAAGATTCTAGGCGAGGGTGTCGTTCGAATCCACGCGGCCAAATATCACGTCC
     G  M  F  S  E  L  R  P  H  R  E  F  G  R  P  W  I  D  R  G

481 TGGTGAACATTCGTGAGTAGAGTCCCGCGACCTACGGGAAAACTCTCGTGATGGCGACAC
     P  S  C  E  H  T  S  D  R  R  S  F  E  R  S  P  S  V

541 GGGTCTCCGGTCGTTATCTCTGCGGGCTGATGCCGCAAGAAGACTCGCATACTTCTCGAA
     P  R  R  D  N  D  R  R  A  S  A  A  L  L  S  A  Y  K  E  F

601 TGGGACATAGACCATATCTTCACGAGATGCGAAGCGGTGAAGCTCCGTTTTTGTTTGCAA
     P  V  Y  V  M  D  E  R  S  A  S  P  S  A  G  N  K  T  Q  L

661 GAACTGGCCCGGAGCATGTCGCCCGACTCCATGGCTGGAACGTGTGTTTGCCCGACGGTG
     F  Q  G  S  C  T  A  S  E  M  A  P  V  H  T  Q  G  S  P  Q

721 CTGACTCTCGCTTATATCGAAGCTTCCTTAATCCCCTATGGTTATTACCTCATTCGC
     Q  S  E  S  I  D  F  S  P  A  T  Q  T  S  V  S  R  D  K  I

781 AGCATTCTCAGGAGTCTCTTCGGAGTGTTCCTTAATCCCCTATGGTTATTACCTCATTCGC
     A  N  E  P  T  E  E  S  H  E  K  I  G  I  T  I  V  E  N  A

841 TTGTAAATATTTCGGGTTGTAAACAGCTGCGTTTCAAACAGGTACC
     Q  L  Y  K  P  N  Y  V  A  A  M  E  R  R  T  K  L  C  T  G

901 CCTATCCATCAAAAACGCCCCGTGAATAAATTCTTCATCAGGACTCGCGTAATTTCTGG
     R  D  M  L  F  A  G  H  I  F  K  K  M  L  V  R  T  I  E  P
```

FIG 7C

```
961  TCGGGACAACTCTCTAGGGACTTCTGCACATTTCTCACGTGTAGCTATTTCATACAGCTG
      R   S   L   E   R   P   V   E   A   C   K   E   R   T   A   I   E   Y   L   Q

1021 TTCTTTAATTGGTGCGCTCAAATCATCAAATGCTCCAATAGCTTCCGAAGCGGTGGCCCC
      E   K   I   P   A   S   L   D   D   F   A   G   I   A   E   S   A   T   A   G

1081 GTAAATTGCTACCGTGCCTTCACGTCTACCCAACTCACAGAGCGCCACGTGTGCAAAAAA
      Y   I   A   V   T   G   E   R   R   G   L   E   C   L   A   V   H   A   F   F

1141 ATCTTTTCCGGGCACTTCGTTCTTTTCAAGCCGCCTTGAAGAGAGCGATAGAGAAGGTAG
      D   K   G   P   V   E   N   K   E   L   R   R   S   S   L   S   L   S   P   L

1201 AATGTTGCTGAGAAGATAGAGAAATTTCTCTGTCTCCGTCAAAACCATCCCCTCTTCCGGC
      I   N   S   L   L   Y   L   F   K   E   T   E   T   L   V   M   G   E   E   A

1261 ATTCGCAAAAGAGCATCATCTTGCACGTAGCTTAAAAAATAGGTGCAAGAGCAGTTGA
      N   A   F   L   A   D   D   Q   V   Y   S   L   F   I   P   A   L   A   T   S

1321 CACGACACCCAAACAAAACAGTCCTCTCGGCAGGTCTAAGATCGTCAGCACTGTACCTAC
      V   V   G   L   C   F   L   G   R   P   L   D   L   I   T   L   V   T   G   V

1381 CACGCAGGATGACTCGTGGTCAATGTTTATCGGAATTGTTCCAGGCAAAACTGGTAAAGC
      V   C   S   S   E   H   D   T   N   I   P   I   T   G   P   L   V   P   L   A

1441 CGATTTGCTTTGCTCGGAGTAAGCTCATATTCTCGCCCGGCACTTTCTTGGTGGTCATA
      S   K   S   Q   E   R   T   L   E   Y   E   R   G   A   S   E   Q   H   D   Y
```

FIG 7D

```
1501 TACTACCAAATAGCCGGCAACGAAGATATATTTGATGTGACGTTCTCCGACATAGGAG
        V  V  L  Y  G  A  V  F  I  Y  K  I  D  V  N  E  S  M <<ORF1
1561 ACCGACTCGACCCGCAAAGTATCAACACACTGACAAAACAGGACTGATCAGAAAGAT
1621 ATAACCCTTTTATTGTCTAAACAGAGACGCGATCGCGAAAATACTAAGCATTATCCATAT
1681 GTCACGTGATGTGGCAAGCATCCAAGACACATAAAATAGATCAGGTCAGAATCAGACTCC
                                                     *  V  G
1741 ACGTTGAATGTCCTCAATATTCCTTCAAATGCTTTTTTGCATCAAATACCTCAAGTAA
      R  Q  I  D  E  I  N  R  E  F  A  K  K  A  D  F  V  E  L  L
1801 CCTGGACACTCCCTCTCTTCAACGTCACCTGTCAATGAATCGTGTACCGCCAAAACAGCAGC
      R  S  V  G  E  E  V  D  G  T  L  S  D  H  V  A  L  V  A  A
1861 TGCCCCGCTACCCACATGTGACGTTTTTCTGAGATCAAGCTCAATTAGATTACAGAGGGA
      A  G  S  G  V  H  S  T  K  R  L  D  L  E  I  L  N  C  L  S
1921 GGAATAGTACTCCCCCAACCAGTATTCCTTTAACGCGCCCCGTTATGCA
      S  Y  Y  E  G  L  R  V  A  T  P  I  G  K  V  R  G  T  I  C
1981 GAGTGCAGCTAAACCAGGAAAGAACCAGTAACTTCACATCTGTTGTCATATCTATACAT
      L  A  A  L  G  P  F  F  G  T  V  E  C  R  N  D  Y  R  Y  M
```

FIG 7E

```
2041 AGGTACAACATATTTCTCGAATAAAAAGAACAAGTTGTTGTCGCGACTGGCCATATCTTG
      P  V  V  Y  K  E  F  L  F  E  N  N  D  R  S  A  M  D  Q

2101 TCCATTGTCATCAAATGTGCTTGCGGTGGCTCTTGAGGTCTTGACCCAGGGCGACGGGCCA
      G  N  D  F  T  S  A  T  A  Q  P  R  S  G  P  A  V  P  W

2161 TTTAGCTGCCTCCTGTTCCGATTGGGTTCCAAGTGGCAATTCAAAGAACCGCAGATGGCTG
      K  A  A  E  Q  E  S  Q  T  G  L  P  L  E  F  F  A  S  P  Q

2221 AAATCGATTGAGATGTGTGCTCGTATAGACATTACTATTAAACATTAGCTTTTGCAAGAC
      F  R  N  L  H  T  S  T  Y  V  N  S  N  F  M  L  K  Q  L  V

2281 TAGGAGCAGAGATATCGAGTCTATAACCGTTCGCACAAGCGGATCATCTTCATGAAGAAT
      L  L  L  S  I  S  D  I  V  T  R  V  L  P  D  D  E  H  L  I

2341 TAACGGCGTTCGTCTCGAAGGGAAAAATGAAATGGAGAGAGCAGCAATGGGTCATCAAA
      L  P  T  R  R  S  P  F  F  S  I  S  L  A  A  I  P  D  D  F

2401 ACGAACAAAATCTGGATCTATTGGAAGCAGAGTTTCTTTCGTTATATCTCGTACTGTGGT
      R  V  F  D  P  P  D  I  P  L  L  T  E  K  T  I  D  R  V  T  T

2461 GGAAAGGGTCCCACTACGCTTTAGCAATTGATACACTATGTGAGGATCGAACACTCCATT
      S  L  T  G  T  R  K  L  L  Q  Y  V  I  H  P  D  F  V  G  N

2521 CGAATATTTTCTGCCGTCAATTGGGGAAAAAAGTTTACGGGGAGTTTGACCGGTCAAA
      S  Y  K  R  G  D  I  P  S  F  F  N  V  P  L  K  S  R  D  F
```

FIG 7F

```
2581  TGAAAATGTAACTGAGCCCCACTCGGCCCCGAATATCTTCCAGCATATAATTAAATACGT
        S  F  T  V  S  G  W  E  A  R  I  D  E  L  M  Y  N  L  Y  T

2641  TGGAACATGTCTTAATGCATCTTCAAATATAGAAACATCAAGACCATGTCTAATGTTTGA
        P  V  H  R  L  A  D  E  F  I  S  V  D  L  G  H  R  I  N  S

2701  AGCAGATTGTCTAGACCGCGAGTGCAGTAAGCATAAAACAGTAGCCTCGAATAGCCGTTT
        A  S  Q  R  S  Y  H  L  L  C  L  V  T  A  E  F  G  S

2761  ATATTGTCGAGTCCCAGCATAAATTTCCATCGCCAGCGCTCGAATCGCCAGCGATAGCTTT
        Y  Q  R  T  G  A  Y  I  E  M  A  S  R  L  A  R  I  A  T  K

2821  CATAAACCGCCCGAGATGCGCGTGTCTCCCATTACATTCAAAACCCTAGCGATAGCTTT
        M  F  R  G  S  I  R  T  D  G  M  V  N  L  V  R  A  I  A  K

2881  ATTGTTATCTAGGAGCTGAGTCTGTAGCGCGAAACCAAGACCCGAATCCCAGCCCGGCC
        N  D  L  L  Q  T  Q  L  A  R  F  W  S  G  F  G  L  R  G

2941  ATTGCCAGCAATAGCAAACGAAGTTGTCAGAAAAATCTACTTGAAAAATCTGTATTAAAAGT
        N  G  A  I  A  F  S  T  T  L  F  D  V  Q  F  D  T  N  F  T

3001  TAATGGTTCTCCATTCTTAACTATCCAAATTACGTTCGCAGGGACATCCTCGCCAGGCGC
        L  P  E  G  N  K  V  I  W  I  V  N  A  P  V  D  E  G  P  A

3061  ACGGATGTCTAGTGTTTTATAAGACCCAACAATGTCCTTCCTGCACGGCCCGCTGGGC
        R  I  D  L  T  K  Y  S  G  V  I  D  K  E  Q  V  A  R  Q  A
```

FIG 7G

```
3121 TAAATCATCCAAGACATCAATTACAGTCTCCTAGGGGATATATTCAATAGTTTGCAATGCCGA
       L  D  D  L  V  D  I  V  T  E  L  P  Y  E  I  T  Q  L  A  S

3181 TGAGACATGTACGGGAACAGTAGCGCTCATATTTTCCAGTTGCTCTAAAGCTGCCTTGGC
       S  V  H  V  P  V  T  A  S  M  N  E  L  Q  E  L  A  A  K  A

3241 AGCCCTGTTCCGCCCTTTCCAGATCTTCAATCCTTGCACGATTGGTCATGATTTCTGCGTC
       A  R  N  R  R  E  L  D  E  I  R  A  R  N  T  M  I  E  A  D

3301 TATTAGAGTTCCTTCGAAAAGCTTAGATGCATATATTTACTCGAGCCTTCCGCGCAGGAGAT
       I  L  T  G  E  F  L  K  S  A  Y  K  S  S  G  E  A  C  S  I

3361 AAAGTTTAAACGATCGGCTAAAACCATCAAGGTAGACGGCTTGTGTCCTTTGGTAA
       F  N  L  R  D  A  L  V  M  L  T  S  P  K  N  S  D  K  P  L

3421 ATTCATAGGTTCGAATCTGGGTCGAAACATGGTTCGGACAAGTTTTTGGACTCCTCCGTA
       N  M  P  E  F  R  P  R  F  M  <<ORF 2
                      *  L  N  S  D  P  D  F  C  P  E  S  L  N  K  S  E  E  T  S

3481 GAAGTGGAATAGCTCGCGGGTTTGGTTGCGGACTCTCTTTTCCCACGGCGACGAAAACAAT
       T  S  Y  S  A  P  K  T  A  S  E  K  G  V  R  S  S  F  L  A

3541 GCAGCTACGGTTTGTAAGGCTGAAGGCGGGAGACGCTAGATCCGCATTCTTTGCACTT
       A  V  T  Q  L  A  S  P  A  P  S  A  L  D  A  N  K  A  S  E
```

FIG 7H

```
3601 TCTTGTTGATACTTACTGCGCGCATGCGACACGCGTGGCTCTAATTTCGCGCAGAAAGTC
      Q  Q  Y  K  S  R  A  H  S  V  R  P  E  L  K  A  C  F  T  K

3661 TTTAAATACTGGCTTCTGGTAGCTAGAGTGACAAAGAAAAGCTCAGACGATACATTTATA
      L  Y  Q  S  R  T  A  L  T  V  F  F  L  E  S  S  V  N  I  V

3721 ACCGTTTCCCCAACCGTTTTTACCGCCAAGATGTTCATCCCCCGTTGAGCAACAAATACC
      T  E  G  V  T  K  V  A  L  I  N  M  G  R  Q  A  V  F  V  L

3781 AGTAGAGAAAGAATCTTTACTTTCTCAGTGCCAGTATATCCTTGTCTTAATTACTTTCAGTCATC
      L  S  L  I  K  V  K  E  T  G  P  V  A  L  N  E  L  L  R  A

3841 GCAGAATCGCCGAAGTTGGAGAGTGCCAGTATATCCTTGTCTTAATTACTTTCAGTCATC
      S  D  R  L  Q  L  T  G  T  Y  G  Q  R  L  K  S  E  T  M  L

3901 AAAGATTTGGAAAAAACGACATGTTTTCAGTTCAATCACAATACATTTCATTTCATGTTGT
      S  K  S  F  R  C  T  K  L  E  I  V  I  C  K  M  E  H  Q  T

3961 GTCTCCAGCAAACAAATGCAATCAGGTTTCCGCAACCCTAGGTTCACTTCAAACATGACT
      E  L  L  C  I  C  D  P  K  R  L  G  L  N  V  E  F  M  V  V

4021 ACAATTTTGCCCCCGGCAGTTTGCATTGGGGAATTATCGTATAGGCCAGCCTTCCGTCT
      I  K  G  G  A  P  K  C  Q  P  I  I  T  Y  A  L  R  G  D  G

4081 CCACCCCCTTCAAAGACTTCCTCCAGTGATCTGAGCGAGAGCTCGGTAAAAGGATTATGG
      G  G  E  F  V  E  E  L  S  R  V  L  A  R  Y  F  R  N  H  C
```

FIG 71

```
                ORF 4 >> M  A  V  A  G  A  V  K  T
4141 CAACGGGATTCCGGCATTTAGTCTAGCCCGCAGAGATGGCCGTAGCTGGCGCCGTGAAAAC
       R  I  G  A  N  L  R  A  R  L  S  P  R  L  Q  R  R  S  F  K

S  G  G  V  Q  F  C  S  E  F  E  N  D  D  S  D  F  R  R  V
4201 TTCCGGTGGTGTGCAGTTTTGCTCCGAGTTCGAGAACGATGACTCCGACTTTCGCCGCGT
       R  H  H  A  T  K  S  R  T  R  S  R  H  S  R  E  G  R  Q

V  L  L  Y  D  G  P  F  G  V  G  K  T  V  T  A  K  T  L
4261 TGTACTTCTTTACGTCGACGGGCCATTCGGAGTCGGTAAAACAGTCACTGCAAAGACGTT
       V  E  K  R  R  R  A  M  <<ORF 3

M  Q  M  P  N  W  R  G  C  R  L  Y  L  A  E  P  M  Q  A  W
4321 GATGCAAATGCCAAATTGGAGAGGTTGCCGTCTATACTTAGCGGAACCTATGCAAGCATG
       R  Q  W  F  G  G  A  D  M  I  K  E  I  N  E  I  Q  T  L  K

4381 GCGCCAATGGTTTGGCGGAGCGGATATGATCAAAGAAATTAATGAAATACAAACCCTAAA
       A  S  G  K  L  E  C  R  E  A  S  P  V  A  V  A  E  V  Q  M

4441 GGCTTCCGGAAAACTTGAATGTCGGGAGGCGTCTCCGGTTGCCGTAGCGGAAGTTCAGAT
       T  I  A  A  P  L  R  I  M  N  H  V  I  Y  N  Y  L  G  S  E

4501 GACTATTGCTGCCCCACTAAGAATAATGAACCACGTCATTTATAATTATTTGGGATCTGA
       R  C  Y  S  A  A  A  S  G  P  D  D  V  L  F  L  V  D  R  H

4561 ACGCTGCTACAGCGCCAGCTGCATCCGGACCAGATGATGTCTTATTCCTCGTAGATAGGCA
```

FIG 7J

```
       P  L  A  A  C  L  C  F  P  V  A  Q  Y  L  S  G  A  L  E  F
4621   CCCACTCGCGGCATGTTTGTGTTCCCTGTTGCACAATATCTAAGCGGAGCGCTCGAATT

G  D  L  I  T  L  L  S  G  I  P  D  I  P  T  H  S  N  I  V
4681   TGGAGATTAATAACTTTATTGTCAGGAATTCCTGACATTCCAACACACTCCAACATTGT

L  M  D  L  D  I  C  E  Q  A  R  R  I  Q  R  G  R  P  G
4741   TTTAATGGATTTGGATATTGCGAAACAGGCACGGCGTATAATACAAAGGGGGCGCCCAGG

E  T  V  D  W  T  Y  L  C  A  L  R  N  S  Y  I  C  L  M  N
4801   GGAAACGGTCGACTGGACGTATTTGTGTGCATTACGTAACTCGTACATCTGCCTCATGAA

T  T  T  Y  L  Q  R  T  S  Y  P  A  L  L  K  E  Q  E  A  L
4861   TACTACCACCTACCTCCAACGTACATCTTATCCAGCATTGTTGAAGGAGCAAGAAGCCTT

T  S  A  T  L  K  F  K  R  E  C  L  E  T  A  T  V  P  E
4921   AACAAGTGCCACGCTCTTAAAATTCAAGAGAGAGTGCTTAGAAACTGCTACTGTTCCAGA

I  N  P  S  I  D  Q  T  L  F  A  I  L  A  F  D  Q  Q  N  V
4981   AATCAATCCTTCAATCGACCAGACGCTATTTGCAATATTAGCTTTTGATCAGCAAAATGT

H  G  E  R  L  K  T  V  L  S  F  V  V  Q  K  L  A  T  V  L
5041   TCACGGGGAAAGATTAAAAACTGTACTTTCATTTGTGGTTCAAAAACTCGCGACGGTATT

K  N  L  C  I  F  Y  L  P  A  H  G  L  T  P  E  A  C  A  L
5101   GAAAAACTTGTGCATTTTTACTTACCAGCACATGGCCTCACCCCGAGGCATGTGCACT
```

FIG 7K

```
          K   C   L   E   F   A   E   T   A   S   S   L   T   T   K   R   A   A   I   A
5161 GAAATGTTTAGAGTTGCCGAGACGGCAAGTTCTCTTACAACCAAACGAGCGGCGATCGC

S   L   I   D   A   V   E   R   Y   N   A   D   M   G   S   *
5221 GAGCTTAATTGACGCAGTAGAGCGCTACAATGCTGATATGGGTTCGTAATGTTCCGCTTC

M   S   F   T   H   F   L   A   L   Y   S   F   L
5281 CATAATCCTTCACAATAAGAGTATGTCCTTTACTCATTCCTTGCTTTGTACTCATTCTT

L   E   R   A   W   L   H   Q   Q   P   A   P   M   G   H   A   R   E   I   F
5341 ACTCGAGAGAGCGTGGCTTCACCAGCAACCCGCCCGATGGGACACGCGAGAGAAATATT
```

Figure 9 ILTV gB

```
  V   L   I   S   N   W   R   Q   C   C   R   R   A

Figure 10 ILTV Ribonucleotide reductase.

HVT HOMOLOGUES OF VZV62/ HSV-1 IE 175

HVT HOMOLOGUE OF RIBONUCLEOTIDE REDUCTASE (LARGE SUBUNIT)

```
Q   V   T   E   V   S   E   G   F   A   P   L   F
CAAGTGACCGAGGTTAGCGAAGGATTTGCCCCTTTGTTCA
         10        20        30        40

S   N   M   F   S   K   V   T   S   A   G   E   L   L
GTAACATGTTCAGCAAGGTGACAAGTGCCGGGGAACTGCT
         50        60        70        80

R   P   N   S   Q   L   M   R   E   L   R   Q   I
TAGACCCAACAGTCAATTAATGCGGGAGCTGAGACAAATA
         90       100       110       120

Y   P   D   N
TATCCCGATAAT
        130
```

FIG. 13A

MDV HOMOLOGUE OF RIBONUCLEOTIDE REDUCTASE ( LARGE SUB-UNIT )

```
   G   I   M   E   G   S   D   V   P   T   E   K   S
GGGGATAATGGAAGGAAGTGATGTACCGACGGAAAAATCT
              10           20           30          40

H   S   G   R   E   R   N   R   S   M   G   I   G
CATTCTGGCCGAGAACGTAACAGATCGATGGGCATCGGCG
              50           60           70          80

V   Q   G   F   H   T   A   F   L   S   M   G   L   D
TGCAGGGCTTTCATACAGCTTTTCTATCTATGGGTCTTGA
              90          100          110         120

L   C   D   E   R   A   R   S   L   N   K   L   I
TTTATGCGATGAACGCGCTAGATCCCTCAACAAGCTAATT
             130          140          150         160

F   E   F   M   L   L   E   A   M   T   V   S   C
TTTGAATTCATGTTATTGGAGGCGATGACAGTTAGTTGCG
             170          180          190         200

E   F   C   E   R   G   L   P   P   F   A   D   F   S
AATTCTGCGAACGGAGGCCTGCCGCCGTTTGCTGATTTCTC
             210          220          230         240
```

FIG 13B

```
  N  S  Y  Y  A  R  G  R  L  H  F  D  G
TAACAGTTATTATGCACGAGGACGTCTGCATTTCGATGGG
         250          260          270          280

W  A  N  V  E  L  A  A  V  E  E  W  N
TGGGCTAATGTAGAATTGGCTGCAGTGGAAGAGTGGAATA
         290          300          310          320
```

FIG 14

MDV HOMOLOGUE OF RIBONUCLEOTIDE REDUCTASE ( SMALL SUB-UNIT )

```
      L  D  V  E  A  I  L  C  Y  V  R  Y  S
      TATTGGATGTTGAAGCAATATTATGTTACGTTACAG
                 10        20        30        40

R  G  Q  T  E  R  I  D  M  P  P  I
      CCGCGGACAGACTGAAAGAATAGATATGCCACCTATT
                 50        60        70        80

Y  N  E  P  K  P  T  A  D  F  P  H  A  L
      TACAACGAACCTAAACCTACACAGCTGATTTTCCGCATGCAC
                 90       100       110       120

T  A  S  N  N  T  N  F  F  E  R  R  N
      TGACAGCTTCAAATAATACCAACTTCTTTGAGAGAAAA
                130       140       150       160

T  A  Y  S  G  S  V  S  N  D  L  *
      TACTGCATATACTCTGGAAGCGTGTCAAACGATCTTTAA
                170       180       190
```

FIG 15

HOMOLOGUE OF HSV-1 IE-175

```
 P   I   P   Y   V   E   E   M   K   D   Y   A
CCCATTCCCGTCTATGTAGAGGAAATGAAAGATTATGCCA
         10          20          30          40

K   Q   Y   D   A   L   V   N   S   L   F   H   K   S
AACAATACGACGCTCTCGTAAACTCTTTGTTTCACAAAAG
         50          60          70          80

M   K   V   N   P   L   N   W   M   H   H   G   K
CATGAAAGTAAATCCCTCTGAACTGGATGCACCACGGGAAG
         90         100         110         120

L   S   T   A   D   A   A   L   N   H   I   Y   V
CTGTCTACCGCCGATGCTGCCCTAAACCACATATATGTTC
        130         140         150         160

Q   K   F   Q   S   S   Y   D   S   P   G   A   A   V
AGAAATTCCAGAGTTCATACGATTCGCCCGGAGCGGCTGT
        170         180         190         200

T   G   T   V   N
AACTGGCACAGTTAACA
        210
```

FIG 16

MDV HOMOLOGUE OF HSV-1 IE-68

```
   S  D  Q  D  F  E  L  N  N  V  G  K  F
 CGTCCGATCAAGACTTTGAACTTAATAATGTGGCAAATT
         10        20        30        40

C  P  L  P  W  K  P  D  V  A  R  L  C
TTGTCCTCTACCATGGAAACCCGATGTCGCTCGGTTATGT
         50        60        70        80

A  D  T  N  K  L  F  R  C  F  I  R  C  R
GCGGATACAAACAAACTATTTCGATGTTTATTCGATGTC
         90        100       110       120

L  N  S  G  P  F  H  D  A  L  R  R  A
 GACTAAATAGCGGTCCGTTCCACGATGCTCTTCGGAGAGC
         130       140       150       160

L  F  D  I  H  M  I  G  R  M  G  Y  R  L  N
ACTATTCGATATTCATATGATTGGTCGAATGGGATATCGACTAAA
        170       180       190       200
```

VIRAL NUCLEOTIDE SEQUENCES

This is a divisional of application Ser. No. 08/125,039 filed Sep. 22, 1993, now U.S. Pat. No. 5,906,821 which is a continuation of Ser. No. 07/669,391, filed Apr. 29, 1991, now abandoned, which is a 371 of PCT/GB89/01075 filed Sep. 13, 1989.

The present invention relates to viral nucleotide sequences which may be manipulated to provide vaccines against disease.

BACKGROUND AND DESCRIPTION OF PRIOR ART

Herpesviruses are large double stranded DNA viruses consisting of an icosahedral capsid surrounded by an envelope. The group has been classified as alpha, beta and gammaherpesviruses on the basis of genome structure and biological properties [Roizman, B et al (1981) Inter-virology 16, 201–217]. Avian herpes viruses include Marek's Disease Virus (MDV) (a gammaherpesvirus) which causes a lymphomatous disease of considerable economic importance in chickens [reviewed in Payne, L. N. (ed) Marek's Disease (1985), Martinus Nijhoff Publishing, Boston] and Infectious Laryngotracheitis-Virus (ILTV) (an alphaherpesvirus) which causes an acute upper respiratory tract infection in chickens resulting in mortality and loss of egg production.

A recent unexpected finding in out laboratory is that there is sufficient amino acid homology between MDV, ILTV and mammalian herpesviruses, particularly varicella zoster (VZV) and Herpes Simplex Virus (HSV) to allow identification of numerous conserved genes. These include the MDV and Herpesvirus of Turkeys (HVT) homologues of glycoproteins gB, gC and gH of HSV; the ILTV, MDV and HVT homologues of TK and ribonucleotide reductase genes and the ILTV homologue of gB and genes 34 and 35 of VZV (Buckmaster, A et al, (1988) J. gen. Virol, 69, 2033–2042.

Strains of MDV have been classified into three serotypes. Type 1 comprises pathogenic strains and their attenuated derivatives. Type 2 are a group of naturally-occurring non-pathogenic strains and type 3 is HVT. For more than a decade, vaccination with HVT has been remarkably effective in controlling Marek's disease. However, in recent years, new strains of MDV have been isolated which cause disease despite vaccination with HVT. Losses due to these 'very virulent' strains have occurred in parts of the U.S.A., Europe and the Middle East. Although the degree of protection can be improved by using a mixture of HVT, type 2 MDV and attenuated derivatives of very virulent strains for vaccination, the results have been erratic,. These observations and the fact that there are MDV type-specific epitopes that are not shared by HVT or type 2 MDV have led us to the conclusion that improved-vaccines might be constructed which are antigenically more related to MDV than existing vaccines. [Reviewed by Ross and Biggs in Goldman J. M. and Epstein M. A. (eds) Leukaemia and Lymphoma Research, Vaccine Intervention against Virus-Induced Tumour, p 1331, Macmillan, 1986].

Infectious laryngotracheitis is also a worldwide problem. Sporadic outbreaks occur in which the severity of clinical symptoms varies considerably. Virus can persist in birds that have recovered and may be shed at intermittent intervals after recovery. An attenuated field strain is currently used as a vaccine. However, it has retained some degree of pathogenicity. Mortality due to the vaccine may reach 10% in young chicks.

A number of herpesvirus antigens have been shown to confer protective immunity when expressed in a recombinant vaccinia virus. These include the gB gene of HSV [Cantin E. M. et al (1987) Proc. Natl. Acad. Sci. U.S.A. 84, 5908–5912], gD of HSV [Paoletti, E. et al (1984) Proc. Natl. Acad. Sci. U.S.A. 81, 193–197] and gp50 of pseudorabies virus (PRV), a homologue of HSV gD [Marchioli, C. C. et al (1987) J. Virol. 61, 3977–3981]. Because of the absolute requirement of gB for virus penetration and infectivity and because it is conserved among herpes-viruses, gB and its homologues are important immunogens. Moreover, the presence of gB at the surface of infected cells has been shown to be an important target for humoral and cell-mediated immune responses [Blacklaws, B. A. et al J. gen. Virol. 68, 1103–1114 (1987); McLaughlin-Taylor, E. et al (1988) J. gen. Virol. 69, 1731–1734]. The recently described glycoprotein gH of RSV is also essential for infectivity and may also be an important immunogen [Desai, P. J. et al (1988) J. gen. Virol. 69, 1147–1156]. It has also been shown that gIII of pseudorabies virus (PRV), a homologue of gC, is a major target for neutralizing antibody and for cytotoxic T cells although it is a non-essential protein. Also of interest is the unexpected participation of immediate early proteins in T cell mediated cytotoxic reactions in cells infected with cytomegalovirus (CMV) [Kozinowski U. H. et al (1987) J. Virol. 61, 2054–2058]. Similar antigens could play an important role in the rejection of latently infected and transformed lymphocytes in Marek's disease since immediate early RNA transcripts have been detected in lymphoblastoid cell lines established from Marek's disease tumours.

Although many recombinant vaccines have been constructed using the poxvirus vaccinia as a vector, there are also reports of the use of herpesviruses as vectors for the expression of foreign genes. Thus hepatitis antigen has been expressed in HSV [Shih, M. F. et al (1984) Proc. Natl. Acad. Sci. U.S.A. 81, 5867–5870] and human tissue plasminogen activator has been expressed in PRV [Thomsen, D. R. et al (1987) Gene 57, 261–265. In both cases, foreign genes were inserted in cloned fragments of non-essential herpes genes which were then introduced into the virus vector by homologous recombination. The hepatitis virus gene was fused to a herpesvirus promoter and the recombinant DNA was inserted within the TK gene of HSV. Homologous recombination following co-transfection of the recombinant DNA and wild-type HSV DNA resulted in TK- virus clones that expressed the hepatitis antigen.

In the case of PRV, the gX gene mapping in $U_s$ was used as the site for insertion of the foreign gene. The strategy used involved insertion of the TK gene of HSV in the gX gene of a PRV mutant that had a defect in its TK gene resulting in a TK positive virus. The human tissue plasminogen activator gene was then inserted within a cloned fragement of HSV TK and the recombinant was introduced into the PRV mutant by homologous recombination. TK- virus was selected which expressed the human gene (Thomsen et al as above). Similarly, VZV has been used as a vector (Lowe et al (1987) Proc. Natl. Acad. Sci. U.S.A. 84, 3896–3900].

Several herpesvirus genes have also been shown to be associated with virulence and to be non-essential for growth in vitro. These include the TK genes of HSV [Jamieson, A. T. et al (1974) J. gen. Virol. *24, 465–480;* Field, H. and Wildy, P., (1987) J. Hygiene (Cambridge) 81, 267–277] and of PRV. Indeed it has long been known that PRV is readily attenuated by deletion or TK activity [Tatarov, G. (1968) Zentralbl. Vet. Med 15B, 848–853]. Furthermore, attenuation of the Bartha strain of PRV has been attributed to a defect in gI, a non-essential structural glycoprotein mapping in $U_s$ [Mettenleiter, T. et al (1987) J. Virol. 61, 4030–4032].

Genes of HSV mapping in the internal repeat region (TRS) flanking the long unique sequence have also been associated with pathogenicity [Rosen, A. et al (1986) Virus Research 5, 157–175; Thompson, R. L. et al (1983) Virology 131, 180–192]. Several additional genes of HSV have been shown to be non-essential for growth in vitro although it is not known whether they are associated smith virulence. These include UL24 (Sanders, P. G., (1982), J. gen. Virol. 63, 277–295, large subunit of ribonucleotide reductase (Goldstein D. J. and Weller, S. K. (1988) J. Virol. 62, 196–205), gC (Draper K. G. et al (1984) J. Virol. 51, 578–585), dUTPase (Fisher, F. B. & Preston, V. G. (1986) Virology 148, 190–197), and $U_L55$ and $U_L$ 56 (MacLean, A. R. & Brown, S. M. (1987) J. gen. Virol. 68, 1339–1350).

Moreover there is evidence that several genes of HSV mapping in $U_s$ are also non-essential for growth in vitro [Weber, P. C. et al (1987) Science 236, 576–579].

SUMMARY OF THE INVENTION

One aspect of the present invention provides a nucleotide sequence substantially free of the sequences which would adjoin it in the wild-type virus associated with the sequence, the sequence being selected from the group consisting of:

(a) the HVT homologue of the HSV gB gene, (b) the HVT homologue of the HSV gC gene, (c) the HVT homologue of the HSV gH gene, (d) the TK gene of ILTV, (e) the ILTV homologue of the HSV gB gene, (f) ORF2 of ILTV, (g) ORF3 of ILTV, (h) the ribonucleotide reductase (large subunit) gene of ILTV, (i) the ribonucleotide reductase (large subunit) gene of ffVT, (j) the ribonucleotide reductase (small subunit) gene of MDV, (k) the ribonucleotide reductase (large subunit) gene of MDV, (l) the HVT homologue of the immediate early gene IE-175 of HSV-I, and (m) the HVT homologue of the immediate early gene IE-68 of HSV-I, and minor variations thereof.

Each of sequences (a) to (m) may be associated with further elements such as suitable stop and start signals and other 5' and 3' non-coding sequences, including promoters, enabling expression of the sequence. Such further elements may be those associated with the sequence in its naturally-occurring state or may be heterologous to that sequence.

In particular the promoter may be one associated with one of the sequences (l) and (m) above.

The term "minor variations thereof" is intended to include changes in the nucleotide sequence which do not affect its essential nature, for example minor substitutions of nucleotides for one another. In the case of sequences which are intended for insertion into a vector to encode an antigen, the "essential nature" of the sequence refers to the (glyco) protein encoded. Conservative changes in the nucleotide sequence which give rise to the same antigen will clearly be included, as will changes which cause conservative alterations in the amino acid sequence which do not affect adversely the antigenic nature of the antigen, in particular, antigenic portions of the antigen sequences may be used alone, for example the regions corresponding to nucleotides 273–320 or 867–926 of HVT gH and minor variations thereof. These sequences and the peptides encoded thereby form a further aspect of the invention. In the case of a sequence which is an insertion site, it is necessary only that the sequence should be non-essential for the infectivity and replication of the virus and have sufficient homology with the defined sequence to enable recombination to occur. Thus an insertion of one nucleotide into the sequence could completely change the reading frame from then on in a downstream direction. In the case of an antigen-encoding sequence this would usually alter the amino acid sequence undesirably (depending on where the frameshift occurred), but in the case of an insertion site, the degree of homology would be almost the same, thereby allowing recombination to take place with almost the same ease.

Generally speaking, in an insertion site, if a nucleotide homology of at least 75% is present, the sequence is regarded as a "minor variation". Preferably, the sequence is at least 80, 85, 90, 95 or 99% homologous.

It will be appreciated that such degrees of homology relate to substantially the entire portion of each sequence (a) to (m) defined above. Shorter sequences may be used as probes in the identification or isolation of such longer sequences, but in this case the degree of homology will in general need to be greater in order to ensure accurate hybridisation.

Thus, a further aspect of the invention provides sub-sequences of at least 13 nucleotides having at least 90% (preferably 95%, 99% or 100%) homology with at least one portion of any of the said sequences (a) to (m) above.

In the above list, sequences (a) to (c), (e), (f), (l) and (m) are useful for expressing viral antigens. Sequences (b), (d) and (g) to (k) and, in addition, the TK region of MDV are useful as non-essential sites suitable for insertion of antigen-expressing genes. Thus, sequence (b) is useful for both functions.

The sequences may readily be isolated from naturally-occurring ILTV, HVT and MDV viruses, using the sequence information given herein and standard techniques, for example involving the preparation of oligonucleotide probles and use thereof to hybridise to the naturally-occurring DNA.

Antigenic ILTV and HVT sequences, i.e. sequences (a) to (c), (e), (f), (l) and (m) above, may be expressed in any suitable host and, in particular, in HVT or MDV. Suitable non-essential sites for insertion of one ILTV sequence include the MDV homologue of the HSV gC gene, the HVT homologue of the HSV gC gene, the TK gene of HVT or MDV, the ribonucleotide reductase (large subunit) gene of HVT or MDV and the ribonucleotide reductase (small subunit) gene of MDV.

A second aspect of the invention provides insertional or deletional mutants of MDV, HVT and ILTV as follows:

(i) for HVT, a mutation in the region homologous to the HSV gC gene or in the ribonucleotide reductase gene or the TK gene, (ii) for MDV, a mutation in the region homologous to the HSV gC gene or in the ribonucleotide reductase (small subunit) gene or in the ribonucleotide reductase (large subunit) gene, (iii) for ILTV, a mutation in the TK genet ORF3 or the ribonucleotide reductase (large subunit) gene.

Each mutation may be in the coding or non-coding sequences of the regions identified.

Such mutant forms of HVT, MDV and ILTV may be used as, or created in the course of preparing, viral vectors for heterologous antigen-encoding sequences, or indeed as vectors for any other sequence which one wishes to express in a fowl in which the vector will replicate. Such sequences include, but are not limited to, (a) to (c), (e), (f), (l) and (m).

By "heterologous", we mean that the antigen-expressing sequence has not previously been found in the same place in relation to the remainder of the viral genome. For example, an antigen-expressing gene might be isolated from a virulent strain of ILTV and inserted into the TK region of a less virulent strain of ILTV; this insertion would be regarded as "heterologous" if it did not result in a naturally-occurring virus.

The heterologous sequence may alternatively be one coding for an antigen associated with any one of the following diseases: avian encephalomyelitis (epidemic tremor), avian influenza (fowl plague), avian leukosis, avian paramyxoviruses other than Newcastle disease (PMV2 to PMV7), avian reovirus diseases (enteric disease, tenosynovitis), chicken anaemia (caused by chicken anaemia agent), coccidiosis, egg drop syndrome (EDS76), fowl pox, infectious bronchitis, infectious bursal disease (Gumboro), inclusion body hepatitis (adenovirus), lymphoproliferative disease of turkeys, Newcastle disease, reticuloendotheliosis in chickens, reticulo-endotheliosis in turkeys, rotavirus enteritis, turkey haemorrhagic enteritis and turkey rhinotracheitis. The sequence may alternatively encode paramyosin (a muscle protein common to all invertebrate parasites) or an antigenic part thereof, somatostatin or a growth-promoting part thereof or an immune regulator.

The vectors in accordance with the invention may provide multivalent vaccine protection. For example, a vaccine comprising ILTV carrying an MDV antigen coding sequence would be expected to protect against ILT and Marek's Disease.

Furthermore, the mutant ILTV viruses themselves are potentially useful in vaccines as attenuated viruses, without necessarily having a heterologous sequence inserted.

A convenient process for preparing the deletional or insertional mutants of the second aspect of the invention comprises simply introducing into a suitable cell, for example by co-transfection, a deletional or insertional mutant version of the appropriate region (for example, the TK region) and either whole viral DNA or a whole virus (for example the wild-type virus). The naked DNA of such viruses has been found to be infectious, provided that it has not been sheared. A calcium phosphate precipitate of the DNA is generally advantageous. Suitable cells include chicken embryo fibroblasts, chicken kidney cells and duck embryo fibroblasts, all preferably grown in sub-confluent monolayers in Petri dishes.

The transfected DNA and the whole viral DNA will then recombine with one another in the infected cells by homologous recombination and the desired recombinants can be screened for, for example by the detection of hybridisation to suitable probes or by an immunoassay using suitable antibodies to the gene product of the region in question.

For homologous recombination to take place, the viral DNA must replicate. At present, no cell-free replication system for MDV, HVT or ILTV is known. However, if such a system becomes available, then the process of the invention could be operated therein. The environment in which the replication and recombination occur is not critical.

The ILTV and HVT regions which were identified above as being responsible for encoding immunologically useful viral antigens can be inserted into suitable vectors, for example into HVT or into other vectors such as fowlpoxvirus, bacteria or fungi. In the case of viral vectors, especially herpesvirus vectors and poxvirus vectors, such insertion can be achieved by recombination between the antigen-encoding sequence, flanked by suitable non-essential sequences, and the vector's genome in a suitable host cell as described above. A promoter which is endogenous to the host will usually be used to control expression of the heterologous (viral antigen-encoding) sequence. In the case of bacteria and fungi, the antigen-encoding sequence may be inserted using known or yet-to-be-discovered techniques of DNA manipulation. A nonpathogenic strain of *Salmonella* may be used as such a host. The heterologous sequence may be inserted into the host's genome or be carried on an independently-replicating plasmid.

The flanking sequences which are used may comprise all, virtually all or less of the region into which the heterologous sequence is to be inserted. If all the region is employed, then the sequence of that region will clearly still be present in the resulting virus, but the function of that region will have been deleted. If less than the whole region is used as flanking sequences, then the result will be a structural as well as functional deletion. Either approach may be used.

Thus, the construction of deletional or insertional mutants of ILTV can yield improved vaccines. Alternatively, the expression of ILTV glycoproteins or other ILTV proteins engineered into HVT, fowl pox or other vectors can constitute effective vaccines.

To prepare a vaccine in which HVT, MDV or ILTV is the virus or vector, the virus is grown in suitable cells such as chick embryo fibroblasts in a standard culture medium which as 199 medium (Wellcome or Flow Laboratories) for 3 to 4 days at about 37° C. The cells are harvested by scraping from the surface of the culture or by trypsinisation and suspended in medium containing 1 mM EDTA or 10% dimethyl sulphoxide and in either case 4% calf serum before storage in liquid nitrogen in sealed ampoules.

For vaccination, typically, day-old chicks are injected intramuscularly with about 1,000 plaque-forming units. Immunity follows within a few days.

It should be noted that MDV and HVT are cell-associated viruses and are infectious only when present in cells. Thus, a vaccine based on such viruses will always include suitable infected cells.

The vaccines of the invention may be used to protect any fowl susceptible to ILTV or HTV, including commercially-reared poultry such as chickens, turkeys, ducks and quail.

BRIEF DESCRIPTION OF THE DRAWINGS

Preferred aspects of the invention will now be described by way of example and with reference to the accompanying drawings, in which:

FIG. 2 (Parts A–R) shows the nucleotide sequence of the gB gene of the RB1B strain of MDV, with the numbering referring to the MDV nucleotides, the sequence of part of the HVT gB gene shown under the line, homologies indicated by vertical bars, and amino acid differences between MDV gB and HVT gB shown above the line;

FIG. 4 (Parts A–H) shows the nucleotide sequence of most of the HVT 9H gene, with the corresponding amino acid sequence shown above the line;

FIG. 5 (Parts A–J) shows the nucleotide sequence of the HVT TK gene, with the numbering referring to the HVT nucleotides, the sequence of part of the MDV TK gene shown under the line, homologies indicated by vertical bars and amino acid differences between MDV TK and HVT TK shown above the line;

FIG. 6 (Parts A–F) shows the nucleotide sequence of the gC gene of the RB1B strain of MDV, with corresponding amino acids shown above the line;

FIG. 7 (Parts A–K) shows the nucleotide and predicted amino acid sequence of a 5400 base pair region of the ILTV genome containing the TK gene cluster. Amino acid sequences predicted for the products of the major open reading frames (ORFs) are indicated in the single letter code below the sequence for the strand and above the sequence for the complementary strand. The locations of potential 'TATA' boxes are underlined. ORF 4 is the ILT TK gene sequence;

Figure 9:
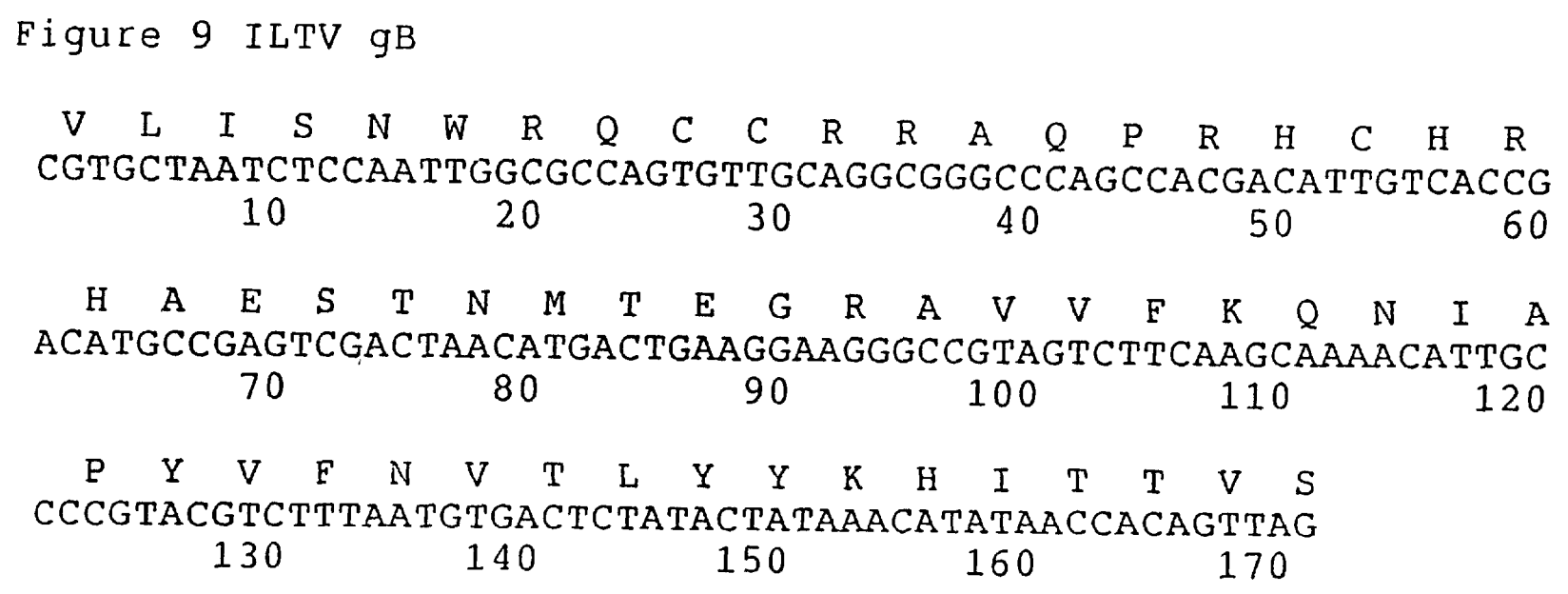

FIG. 9 shows part of the nucleotide sequence of the ILTV gB gene;

Figure 10:
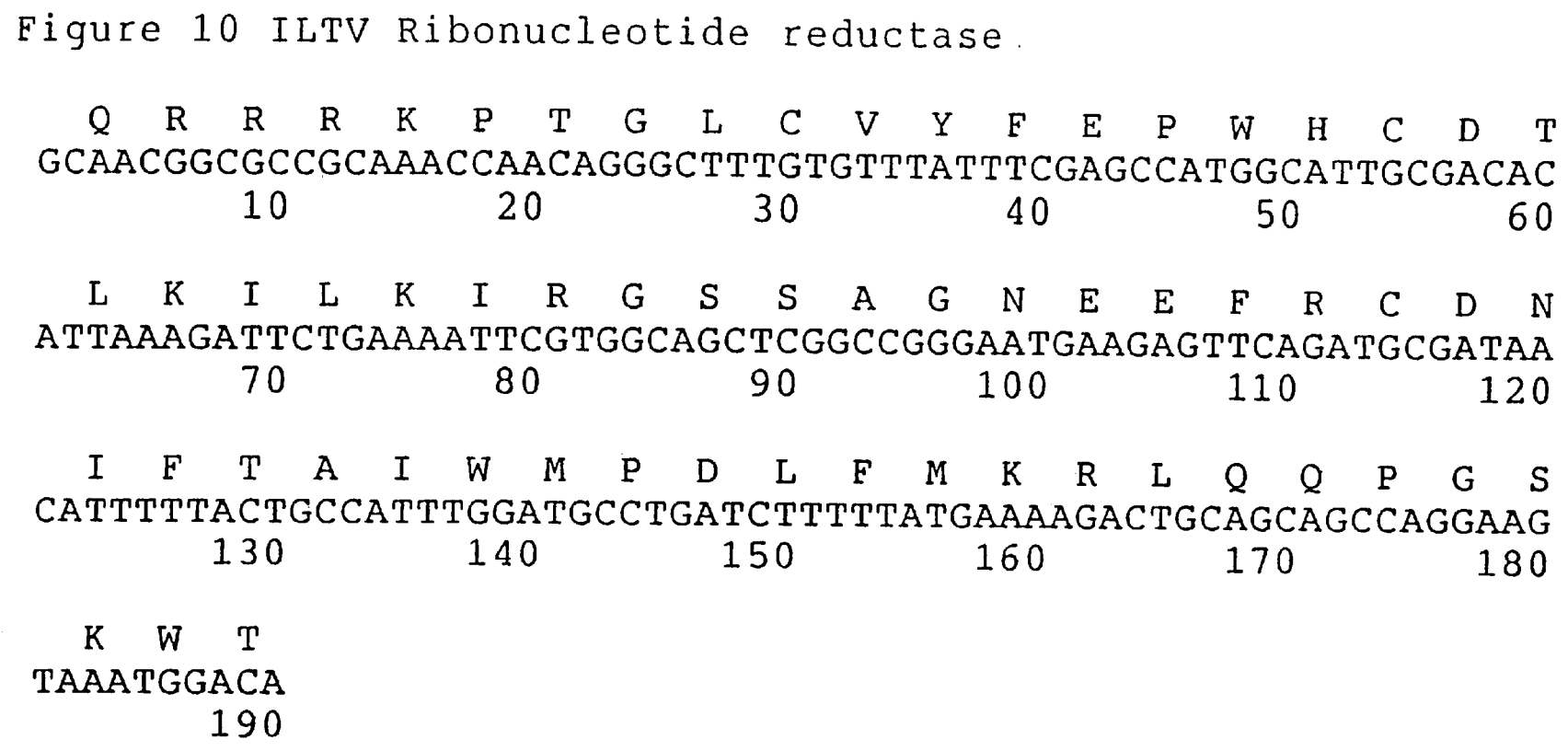

FIG. 10 shows part of the nucleotide sequence of the ILTV ribonucleotide reductase (large subunit);

Figure 11:
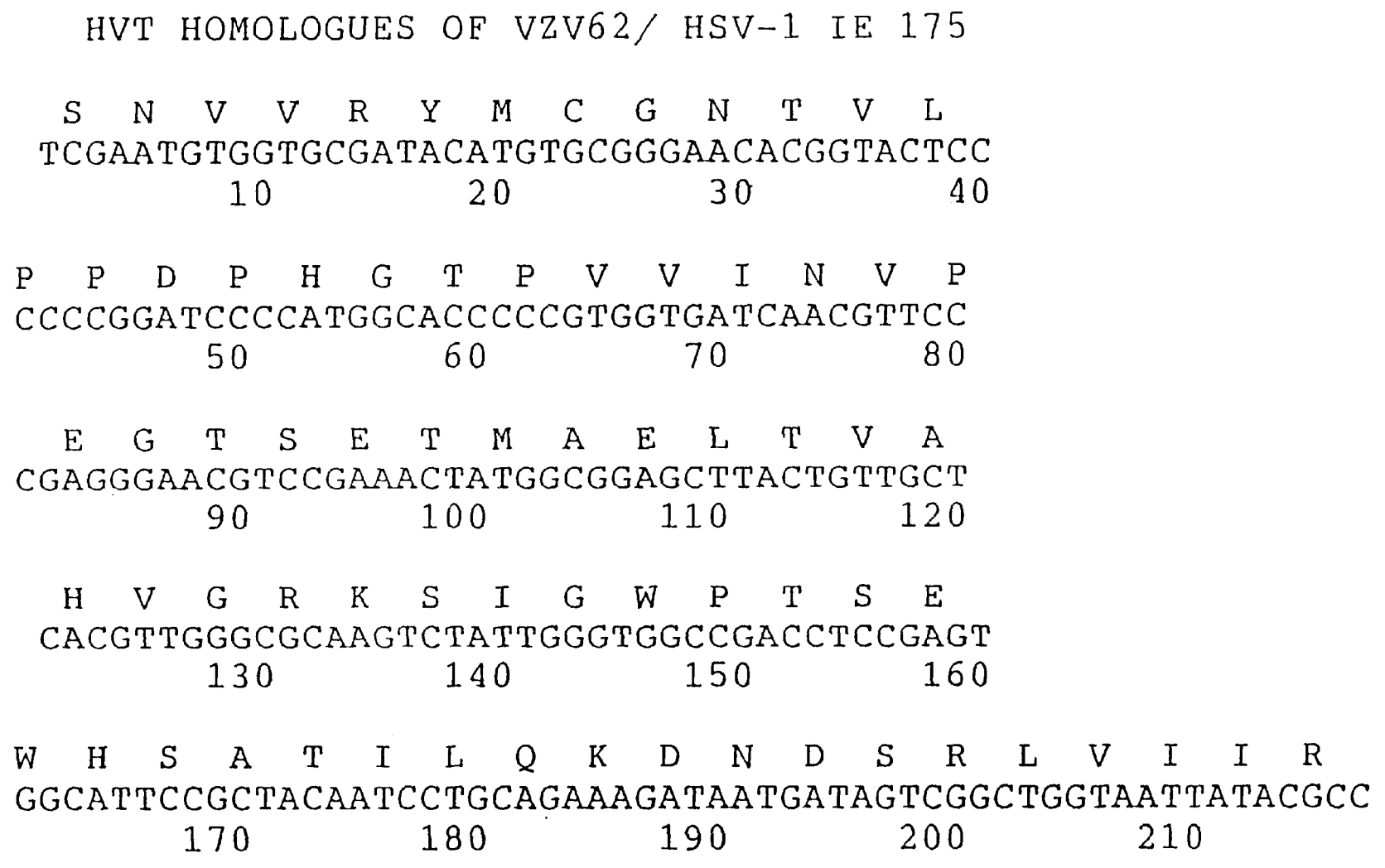

FIG. 11 shows part of the nucleotide sequence of the HVT homologue of the VZV62/HSV-1 IE 175 gene;

FIG. 12 shows part of the nucleotide sequence of the HVT ribonucleotide reductase (large subunit) gene;

FIG. 13 (Parts A–B) shows part of the nucleotide sequence of the MDV ribonucleotide reductase (large subunit) gene;

FIG. 14 shows part of the nucleotide sequence of the MDV homologue of the ribonucleotide reductase (small subunit) gene.

FIG. 15 shows part of the nucleotide sequence of the MDV homologue of the HSV-1 IE-175 gene;

FIG. 16 shows part of the MDV homologue of the HSV-1 IE-68 gene;

EXAMPLES

General Approaches

Figure 1:
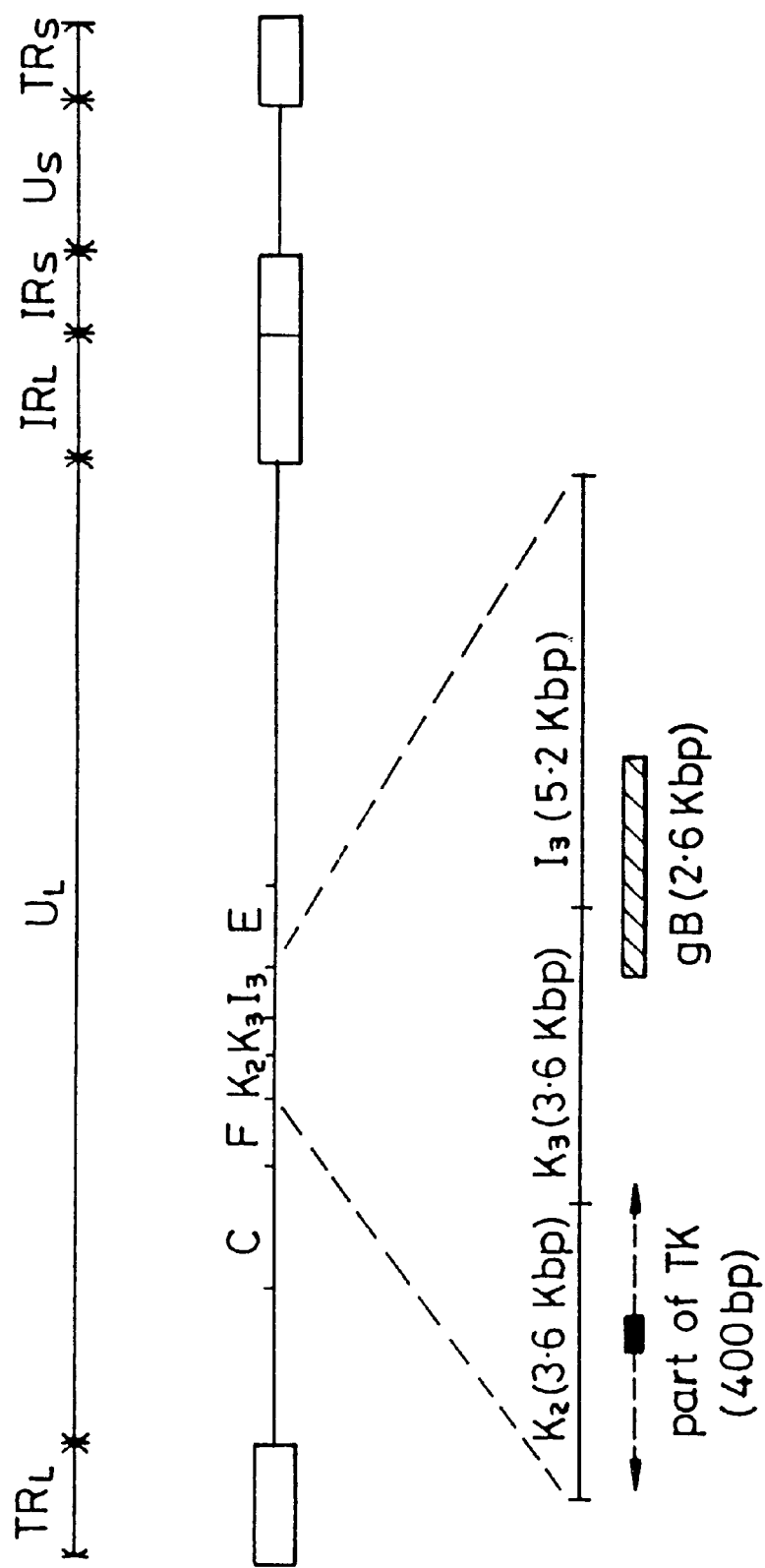
FIG. 1 is a map of the MDV genome showing in part the BamH1 site distribution and the location of the gB and TK genes.

Selected short sequences of the avian herpesviruses cloned in the bacteriophage vector M13 were used as probes to identify longer fragments that might contain the entire genes of interest. This was achieved by Southern blot hybridization of restriction fragments. Full details are given below.

Virus Strains. The 'highly oncogenic' strain RB1B of MDV [Schat, K. A. et al (1982) Avian Pathol. 11, 593–605] was obtained from Professor B. Calnek, Cornell University, Ithaca, U.S.A. The virus received has been plaque purified in chicken kidney vells in tissue culture. It was passaged twice in SPF RIR chickens and 4 times in chick embryo fibroblasts (CEF). Its 'highly oncogenic' nature was demonstrated by a high incidence of gross tumours when inoculated in genetically resistant N-line chickens.

The FC126 strain of HVT [Witter, R. L. et al (1970) Am. J. Vet. Res. 31, 525–538], obtained from the Wellcome Research Laboratories, Beckenham, Kent, had been passaged 14 times in CEF. It was subsequently grown in duck embryo fibroblasts (DEF) and CEF in our laboratory. It was then plaque-purified and grown further in CEF. Viral DNA used for cloning in the present work was extracted from virus that had been passed 29 times since the original isolation.

The Thorne strain of ILTV was passaged twice in eggs, once in chicken kidney cells (CKC) and plaque-purified three times in CKC.

Tissue culture. CEF were grown in roller bottles in 199 medium (Wellcome), supplemented with penicillin, streptomycin, Fungizone (Regd T. M.) and calf serum as described previously [Ross, L. J. N. et al (1975) J. gen. Virol. 28, 37–47].

CKC were grown in 10 cm Petri dishes [Churchill, A. E. and Biggs P. M., (1967) Nature, 215, 528–530).

Isolation of MDV DNA. Cell associated RB1B was inoculated onto confluent monolayers of CEF in roller bottles at a multiplicity of infection of approximately 0.001 plaque-forming units (pfu) per cell, and the cultures were incubated at 37° C. After 3 days, the medium was discarded and replaced with fresh 199 medium containing 2% calf serum. Cells were harvested for virus purification after 2 to 3 days when cytopathic effect was extensive. Virus was obtained by rate zonal centrifugation of the cytoplasmic fraction of infected cells [Lee, Y. S. et al (1980) J. gen. Virol. 51, 245–253]. Viral DNA was extracted by treating purified virus with sarcosyl, proteinase K and Tris buffer pH 9 overnight at 37° C. and purified by rate zonal centrifugation in glycerol gradients as described previously (Lee et al, 1980). High molecular weight viral DNA was precipitated with ethanol and resuspended in 10 mM Tris pH 7.5 im 1 mM EDTA (TE).

Isolation of ILTV DNA. (a) Infected CKC were harvested 2–3 days after inoculation, washed in PBS, and resuspended in ice-cold TE by vortexing. Cells were lysed by addition of the non-ionic detergent NP40 (final 1%) vortexing and incubation on ice for 15 min. After treatment with RNAse, the preparation was centrifuged at 2000 rpm for 5 min in a bench top centrifuge (Centaur). The supernatant was collected and incubated at 37° C. for 30 min in the presence of SDS (final 1%) and proteinase K (final 0.5 mg/ml). The mixture was extracted twice with phenol-chloroform and once with chloroform and the DNA was then precipitated with ethanol and ¹/₁₀ vol of 3M sodium acetate.

(b) Viral DNA was also isolated from the media of virally infected cells in the following way. The media of infected cells were harvested at 2–3 days post infection and centrifuged at 3000 for 5 mins at 4° C. rpm in a bench centrifuge. The supernatant was collected and centrifuged at 19K rpm in an ultracentrifuge (Sorvall) for 1 hr at 40° C. The viral pellet was resuspended in TE, digested with RNAse A, then disrupted with SDS and proteinase K as described above. Finally, DNA was extracted from the disrupted-virus as described above.

Cloning of MDV DNA. One fg of MDV DNA was cut with the restriction enzyme BamH1 and ligated to BamH1-cut, dephosphorylated pUC13 DNA (Pharmacia). Competent E. coli strain TG1 cells were transformed according to standard procedures [Hanahan, D. (1983) J. Mol. Biol. 166, 557–580] and were grown in the presence of ampicillin and X-gal. White colonies were picked and tested for the presence or MDV inserts by hybridization to nick-translated MDV DNA [Grunstein M. and Hogness, D. S. (1975) Proc. Natl. Acad. Sci. U.S.A. 12, 3961]. Positive colonies were cultured in small volume and plasmid DNA isolated by the procedure of Holmes, D. S. and Quigley, M. [(1981) Anal. Biochem. 114, 193–297]. The size of the inserts was determined by electrophoresis of BamH1 digests of the recombinant DNA in agarose gels. Plasmids containing MDV inserts ranging from less than 1 to 18 Kbp were obtained.

Cloning of ILTV DNA. EcoR1 and B1II libraries of ILTV DNA were obtained by cloning digests of viral DNA in pUC13 as described above.

Random sequencing of viral DNA. Sonicated fragments of viral DNA were cloned into SmaI-cut, dephosphorylated M13.mp10 (Amersham International PLC) and plaques containing MDV inserts were identified by hybridization to MDV DNA. The sequence was determined by the dideoxy method [Sanger, F. et al (1977) Proc. Natl. Acad. Sci. U.S.A. 74, 5463–5467] using $^{35}$S dATP).

The same procedure was used to sequence cloned fragments of MDV, HVT and ILTV DNA except that plaques were identified by hybridization to labelled insert so as to avoid colonies containing pUC13 fragments.

EXAMPLE 1 gB gene of MDV

An M13 clone of HVT homologous to the gB gene of VZV and HSV hybridized to BamH1 fragment I3 of MDV (see FIG. 1). Sequencing of this fragment obtained from a BamH1 library of the RB1B strain of MDV showed that two thirds of the gene, starting with the $NH_2$ terminus, was contained within I3. The remainder of the gene was identified in the adjacent restriction fragment K3. FIG. 1 shows the map position of the gene which is 2.6 Kbp long. Its mRNA has been estimated to be approximately 2.8 Kb. The translated protein is 865 amino acids long (FIG. 2). This includes approximately 20 amino acids which may be part of a signal sequence domain. The primary translated sequence of MDV gB has a few features in common with gB of other herpes viruses such as the alignment of cysteine residues and the presence of hydrophobic sequences which are presumably capable of spanning a lipid bilayer [Pellet, P. E. et al (1985), J. Virol. 53, 243–253]. However, MDV gB has only 48% amino acid similarity with gB of RSV and has many unique features such as the insertion of 23 amino acids (residues 1851–1920, FIG. 2) and the presence of extra sites with glycosylation potential. Comparison of the sequence of MDV gB with limited sequence data (702 bases) available for HVT gB (FIG. 2) has shown 76.9% nucleic acid similarity and 87.1% amino acid similarity between these two glycoproteins. Amino acid substitutions in HVT gB compared to MDV gB were particularly marked in a region (residues 1323–1433) equivalent to a domain of HSV gB associated with virus neutralization [Pellet P. E. et al (1985) as above]. Amino acid substitutions between MDV and HVT gB were also noted in other regions of unknown function.

EXAMPLE 2 gH gene of HVT and gH gene of MDV

Figure 3:
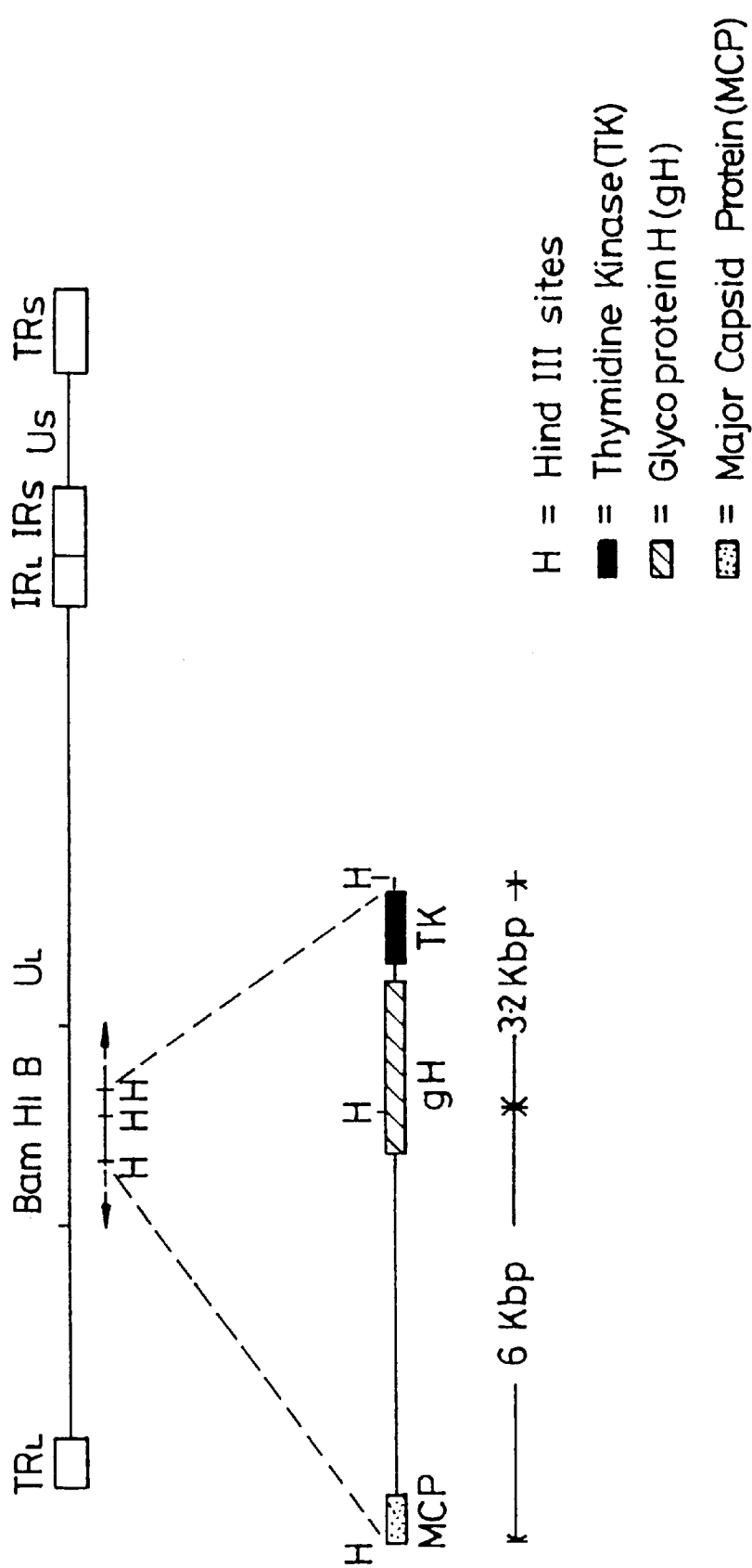
FIG. 3 is a map of the HVT genome showing the positions of the gH (hatched), TK (solid black) and major capsid protein (MCP, dotted) genes, with HindIII sites shown as "H"

An M13 clone of HVT containing sequences homologous to HSV gH was isolated during our earlier work on gene identification and mapping (Buckmaster et al (1988) as above). This clone, when used as a probes hybridized to a 6 Kbp HindIII fragment of HVT (FIG. 3). Sequencing revealed that this fragment contained approximately one quarter of the gH gene including the carboxy terminus. The adjacent HindIII fragment (3.2 Kbp) containing the remainder of the gH gene was identified by hybridization using a cloned HpaI fragment of HVT which overlapped the HindIII site. FIG. 4 shows the sequence of the coding region of the gH gene of HVT (2.3 Kbp) and flanking sequences. The % amino acid identity between the gH gene of HVT and its homologue in HSV1, VZV and EBV was only 20, 24 and 20 respectively (estimated from maximised amino acid overlaps of 630, 644 and 153 respectively).

EXAMPLE 3

TK gene of HVT and TK gene of MDV

The whole coding region of the TK gene of HVT (1053 bp) was contained within the 3.2 Kbp HindIII fragment described above (FIG. 3). The sequence of the entire gene and flanking regions is shown in FIG. 5. Similarly the whole of the MDV TK gene is contained within the 3.6 Kbp BamH1 K2 fragment of MDV (FIG. 1). The sequence of MDV TK gene determined so far is shown in FIG. 5. Comparison of the MDV and HVT TK sequences indicates that the two genes have approximately 60% amino acid identity (estimated from 276 amino acid overlap). By contrast, the % amino acid identities between the TK gene of HVT and the TK genes of HSV 1, VZV and EBV are only 30, 27 and 24 respectively (estimated from amino acid overlaps of 320, 332 and 193 respectively). The predicted amino acid sequences of HVT and MDV TK show characteristic ATP and/or CTP binding site motifs described for a number of virus and eukaryotic proteins that are associated with phosphorylation (Gentry, G. A. (1985) Proc. Natl. Acad. Sci. U.S.A. 82, 6815–6819). These conserved sequences are examples of useful sites for insertion and expression of foreign genes and for producing TK- deletion mutants.

EXAMPLE 4

A antigen gene of MDV (gP57–65) (gC homologue)

The A antigen gene is of interest in vaccine development both as an immunogen (it encodes a major glycopolypeptide product) and also because we have identified it as the homologue of HSV gC, a potential non-essential region. The A antigen gene was mapped within the BamH1 B fragment of MDV (Isfort et al 1987), and the nucleotide sequence determined for the GA strain of MDV (Coussens and Velicer, Abstract OP18.51, VII International Congress of Virology, Aug. 9–14 (1987) Edmonton, Canada; J. Virol. 62, 2373–2379). During the random sequencing studies described earlier (Buckmaster et al 1988), we identified an M13 clone (No. 130) which came from the A antigen gene. This clone was then used to identify a 2.3 Kbp EcoR1/PvuII fragment from the RB1B strain of MDV containing the A antigen. This fragment was cloned into a SmaI/EcoR1 cleaved pUC13 vector by standard protocols. One plasmid (pMB419) was sequenced by the M13 dideoxynucleotide method. The sequence of the MDV RB1B antigen and the predicted amino acid sequence of the protein are presented in FIG. 6. The A antigen regions of MDV and HTV are non-essential genes and they can therefore be used as sites in MDV and HVT into which other genes can be inserted into the virus by homologous recombination. Several lines of evidence support this as outlined below.

1) During our study we isolated and sequenced another RB1B A antigen clone. This had one extra T residue in the string of T's 45 bases 3' to the A antigen ATG codon. This extra T would cause a frameshift which would make it impossible for the gene to encode functional A antigen. As it is probable that this gene was cloned from a replicating MDV, the results suggest that the A antigen is non-essential to the virus.

2) On conducting a similarity search it became clear that the MDV A antigen gene is the homologue of HSV gC and PRV gpIII glycoproteins. Both of these homologous genes are known to be non-essential (for the HSV homologue, see Rosenthal et al (1987) J. Virol. 61, 2438–2447].

3) Strains of MDV lacking A antigen as judged by agar gel diffusion tests [Churchill, A. E. et al (1969) J. gen. Virol. 4, 557–564] or producing low levels using the more sensitive 2D radio-immunoprecipitation (van Zaane, D. et al (1982) Virology 121, 133–146] have been reported.

Furthermore, in view of the fact that the A antigen is a major secreted glycoprotein, it may be a particularly suitable location for the presentation of foreign epitopes within the A antigen as soluble, secreted proteins. This may be achieved by cloning oligonucleotides encoding these epitopes in frame within the A antigen gene.

STRATEGIES FOR INTRODUCING GENES INTO HVT AND ILTV VECTORS

Two possibilities can be envisaged. 1) Insertion into non-essential genes of the vector. 2) Substitution of foreign gene for corresponding gene of the vector. This would be possible only in regions which already have substantial homology as may be the case between some genes of MDV and HVT.

EXAMPLE 5

Insertion into non-essential genes of HVT, ILTV or MDV (a) Insertion at the TK locus of the vector.

1) HVT, ILTV or MDV may be used as vectors for insertion and expression of avian herpesvirus genes. In particular gB, gD, gH or gC of RB1B MDV may be inserted into ILTV. Also gB and BS-17 of ILTV may be inserted into HVT or MDV. One may use the promoter associated with the inserted gene or use heterologous promoters, including those of a different class of genes (for example the immediate early promoter to optimise expression of gB).

2) ILTV may be used as a general vector for the insertion and expression of genes unrelated to avian herpes viruses and likely to require manipulation of promoters for optimal expression.

The procedure to be used for gene insertion is substantially as described previously for the insertion of hepatitis antigen in HSV [Shih et al, 1984 as above].

MDV and HVT DNA obtained as described above is infectious provided that precautions are taken not to shear the DNA during extraction. Calcium phosphate precipitates of viral DNA prepared as described by Stow and Wilkie [(1976) J. gen. Virol. 33, 477] were added to sub-confluent monolayers of CEF. After absorption for 1 h at 37° C., culture medium was added and cultures were incubated for 1 or 2 days until confluent. Monolayers were then trypsinised, replated (1:1 or 1:2) in 199 medium (Wellcome) containing 2 to 4% calf serum and incubated at 37° C. until plaques developed, usually after 4 to 5 days. Approximately 200 plaques may be obtained per µg of HVT DNA and approximately 30 per µg of MDV DNA.

Restriction enzyme sites than could be used for the insertion of foreign antigens into the TK of HVT strain Fc-126 include: BamII, Bsp1286, DraIII, EcoRI, HindII, HpaI, NheI and NsbII.

Some of these enzymes also have sites in the plasmid vector into which the virus DNA fragments are cloned. Thus in order to linearize the clone DNA without also cutting within the vector, partial digests may be carried out.

None of the above enzymes should cause any disruption to flanking gene, HSV-1 homologues of which are known to play an important role in virus multiplication.

For homologous recombination and isolation of recombinant virus, genes of interest are inserted within non-essential genes such as TK or gC and co-transfected with wild-type viral DNA at molar ratios ranging from 10:1 to 2:1 as described above. Alternatively, intact wild-type virus may be used for co-infection.

Virus recombination may be detected by 'plaque lifts' which involve transfer of infected cells and released virus which have adhered to the agar overlay to nitrocellulose and hybridization of the denatured DNA released from the cells and virus to suitable probes as described by Villareal, L. et al (1977) Science 196, 183–185. Virus which hybridizes to the probe may be recovered from the monolayer.

A similar procedure may be used to isolate recombinant virus which expressed epitopes of interest. In this instance the nitrocellulose "plaque lifts" are treated with antibody and the presence of bound antibody revealed using a suitable detection system such as labelled protein A or phosphatase conjugated antiglobulin antibody.

The gene of interest with appropriate promoters is first inserted within the cloned TK gene (FIG. 7). The recombinant DNA is then co-transfected with infectious DNA of the vector in chick embryo fibroblasts or chicken kidney cells and TK- virus may be selected by growth in medium containing acyclovir [Ross, N. (1985) as above] or FMAU [Schat, K. A. et al (1984) Antiviral Research 4, 159–270]. Alternatively, or in addition, plaques are screened for the presence of the gene of interest using 'plaque lifts' on nitrocellulose and hybridization to any relevant labelled probe. Plaques are also screened for expression of the epitopes of interest using monoclonal antibodies or antipeptide antibodies.

The main advantage of this strategy is that the selection procedure increases the chances of obtaining virus recombinants containing the gene of interest. It also offers the opportunity of using different promoters for optimum expression. Thus the use of an immediate early promoter may allow expression in latently infected cells.

(b) Insertion at the gC locus of the vector.

Since the A antigen (HVT and MDV homologues of HSV gC) is not essential for virus growth in vivo and in vitro (see section on gC above) it is a potentially useful site for the insertion and expression of foreign genes. Moreover, since it is one of the most abundant antigens and is excreted, it may be particularly useful for enhancing the immunogenic properties of foreign proteins. The isolation of virus recombinants at this locus may be achieved by first inserting at least part of the gene of interest in frame within the gC gene and then co-transfecting with infectious viral DNA. Screening of virus plaques with sequence specific probes or with specific antibody allows the isolation of recombinants.

EXAMPLE 6

Substitution of ILTV genes for their homologues in HVT

Substitution may be achieved by co-transfection of cloned ILTV sequences and infectious HVT DNA as described in Example 5. Substitution of genes derived from ILTV for their counterparts in HVT may be effected.

Recombinants expressing ILTV sequences and epitopes may be detected using ILTV-specific monoclonal antibodies or anti-peptide antibodies raised against unique ILTV sequences as described above.

The advantage of this procedure is that it is relatively simple and does not require manipulation of promoters. However, it may be limited to genes which share substantial homology.

EXAMPLE 7

Strategies for obtaining TK- mutants of ILTV

Figure 8:
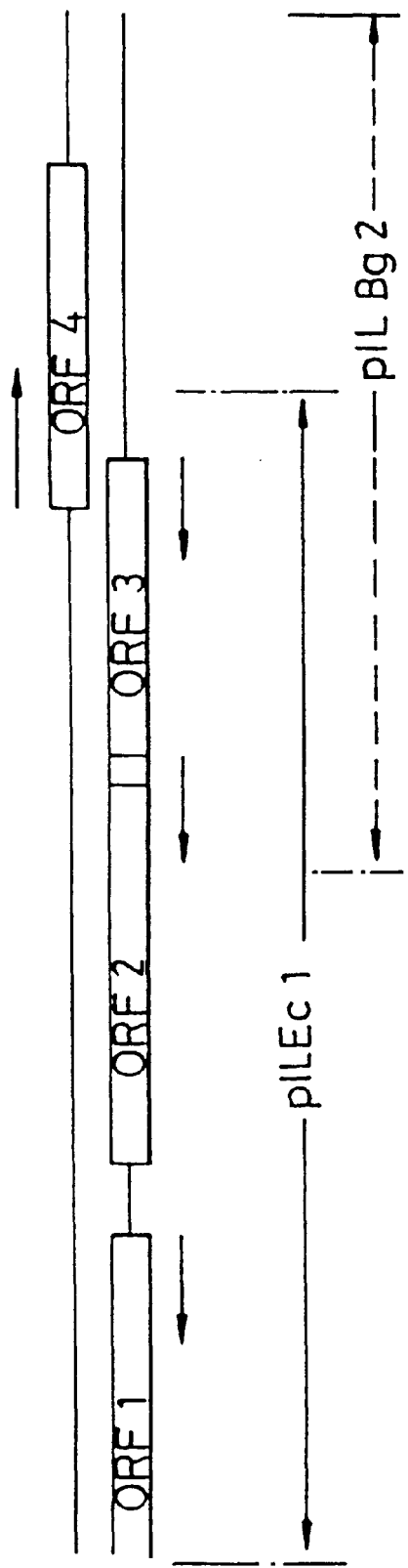
FIG. 8 is a representation of the gene organisation in the TK-containing part of the ILTV genome. Overlapping pUC 13 plasmid clones containing the EcoR1 (pILEc1) and Bg1II (pILBg2) generated fragments of ILTV DNA are indicated. Open reading frames (ORFs) are depicted as open boxes with the direction of transcription indicated by the arrow.
Figure 17:
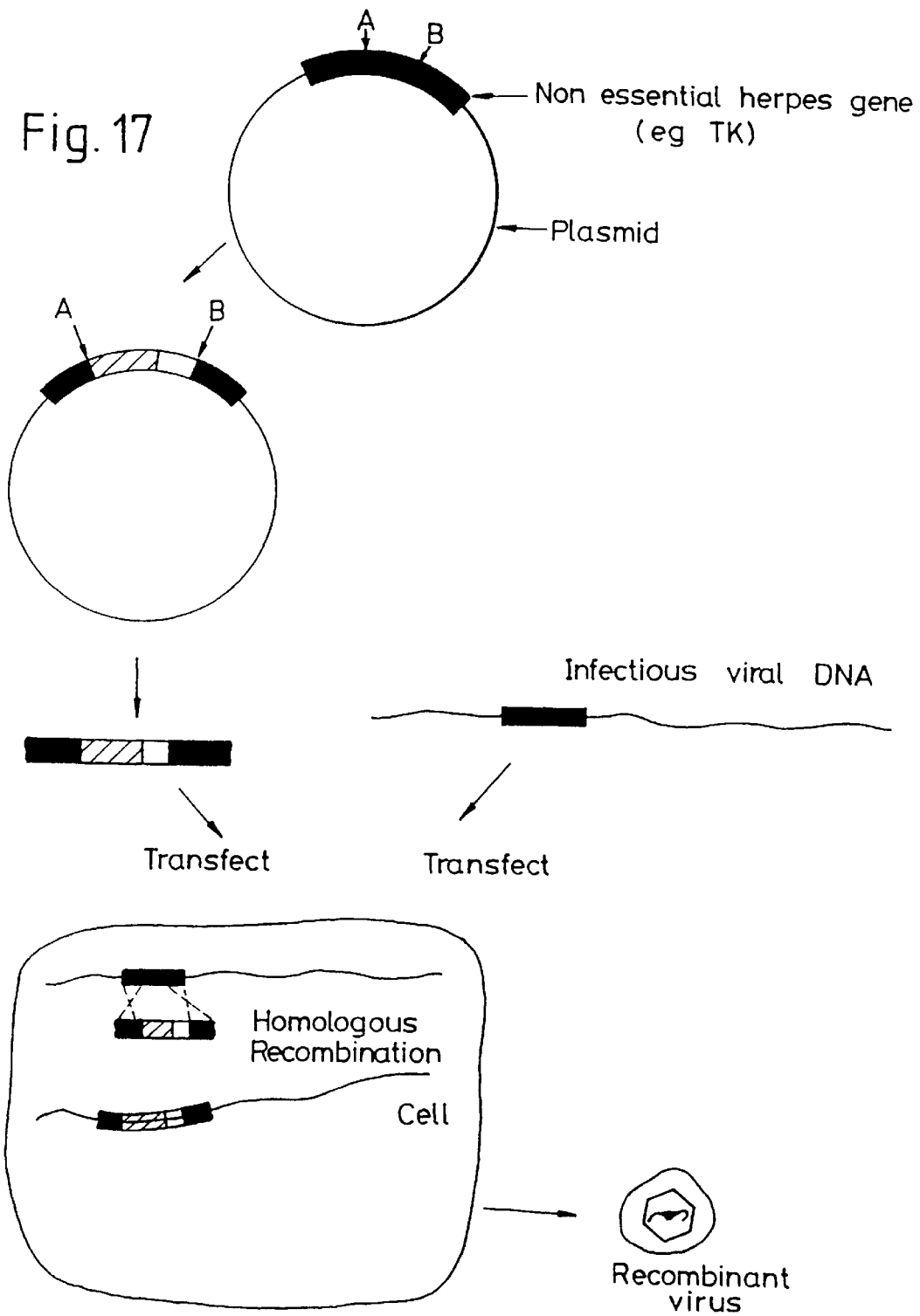
FIG. 17 is a schematic representation of homologous recombination at a non-essential region of a viral genome and a homologous region of DNA cloned within a plasmid vector.
Figure 18:
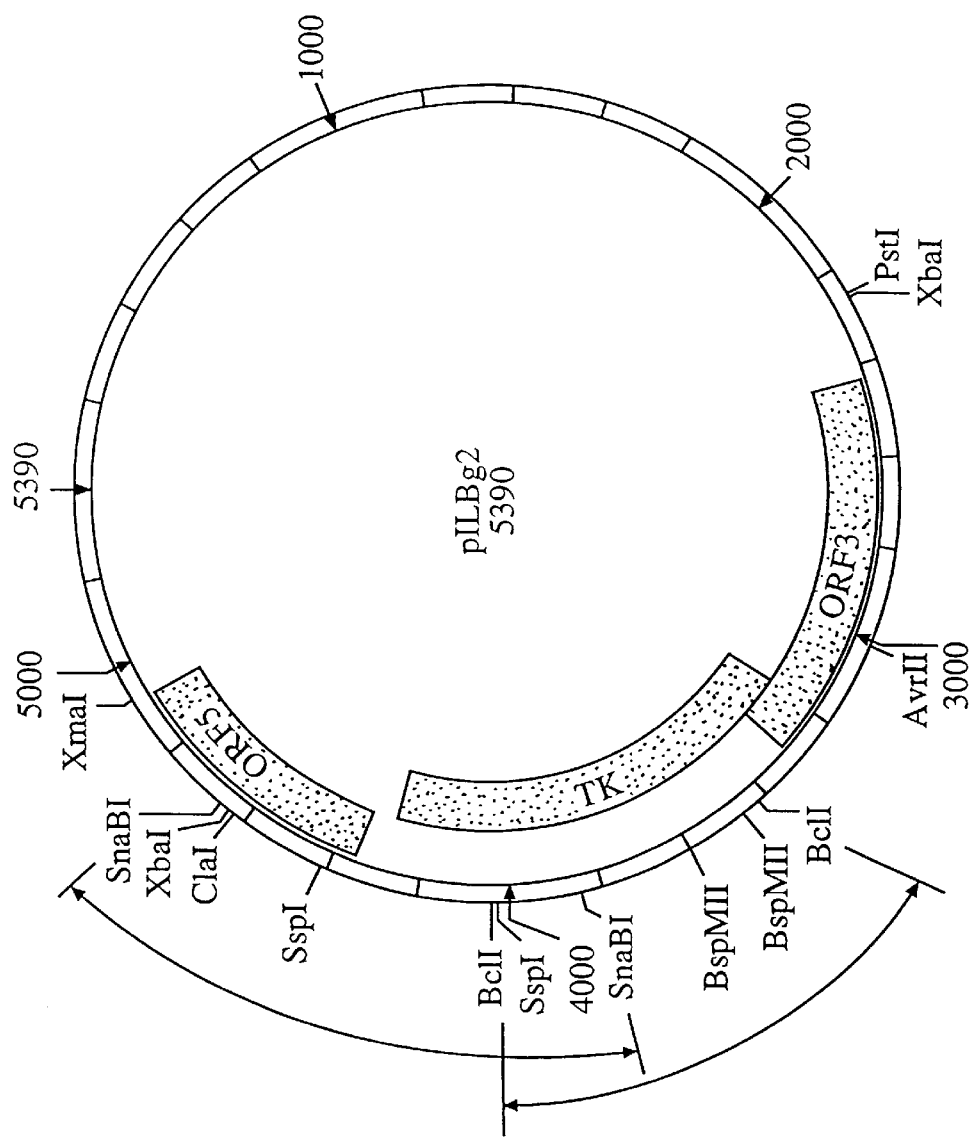
FIG. 18 is a map of plasmid pILBg2, showing restriction sites and the locations of the TK gene and ORFs 3 and 5.

Deletion mutants. Deletions may be introduced within any suitable part of the gene, for example the domains of the gene that are required for its function as a phosphorylating enzyme such as ATP and CTP binding sites. This may be achieved by restriction enzyme digestion for example with SnaB1 or Bcl1, and religation of appropriate fragments followed by co-transfection with infectious viral DNA or transfection into virally-infected cells. Reference may be made to FIGS. 7 and 8, and to the map of plasmid pILBgb2 (FIG. 18), in choosing restriction enzymes and so on. TK- virus may be selected in the presence of acyclovir [Ross, N. (1985) as above] or FMAU [Schat, K. A. et al (1984) as above]. Plaque-purified clones may then be tested for the absence of the deleted portion of the TK gene by hybridization.

The deletion mutants of ILTV may be used themselves as attenuated viruses for vaccine preparation, or may have sequences for heterologous antigens inserted.

Insertional mutants. A functional β-galactosidase gene under the control of a herpesvirus promoter or any other suitable sequence or a single base is first introduced in a domain of the TK gene which is essential for TK activity. The recombinant DNA is then cotransfected with infectious viral DNA or transfected into virally-infected cells to allow homologous recombination to occur. Selection in the presence of acylovir or FMAU will yield TK- insertional mutants. If a β-galactosidase gene is introduced, mutants can be detected by the production of blue plaques in the presence of X-gal.

The TK gene and surrounding sequences may be subcloned into another suitable vector if necessary.

EXAMPLE 8

Insertion of MDV RB1B gB gene into HVT (Not within the scope of the invention, but illustrates an analogous technique).

The HVT TK gene is cloned in the plasmid vector pUC13 to generate a plasmid, which may be termed pTK1B. This plasmid is linearised with, for example, the restriction endonuclease Rsr II which cleaves the plasmid only within the TK gene (nucleotide position 197 in FIG. 5, enzyme recognition sequence CGGACCG). The "sticky" ends thus generated are end repaired by standard techniques (see "Molecular Cloning: a Laboratory Manual", ed. Maniatis T., Fritsch E. F., and Sambrook J. Cold Spring Harbor Laboratory 1982).

The RB1B gB was originally cloned on two plasmids which were termed RB1B-BamH1 -I3 and RB1B-BamH1-K₃. (Note I3 had lost one BamH1 site during cloning.) To generate a complete gB copy on one plasmid, both plasmids were cleaved with BamH1 and the fragments ligated. However, the complete gB gene was later obtained independently on an EcoRI/SalI fragment. Ross et al, J. gen. Virol (1989) 70, 1789–1804 provides further information regarding the manipulation of viral genes. Recombinants containing the desired configuration can be identified by restriction enzyme analysis of plasmid DNA's.

The recombinant plasmid is then cleaved with EcoR1, the ends are repaired and the plasmid is cloned into PTK1B prepared as above. The recombinant plasmid is then introduced into cells containing HVT virus (viral DNA) and homologous recombination will introduce the gB gene into the TK gene. HVT viral recombinants can be selected with acyclovir or FMAU or alternatively detected with labelled gB probes.

EXAMPLE 9

RB1B SC (A antigen) gene into HVT

Blunt ended PTK1B is prepared as in Example 8. The RB1B gC is cleaved from the plasmid pMB419 (Example 4) with the restriction endonucleases EcoR1 and HindIII (site within the pUC13 polylinker). The sticky ends generated are again end-repaired by standard protocols. The end-repaired gC fragment is then cloned into the linearized end-repaired pTK1B as in Example 8. (The cloning can be verified by analysis of the resulting clones with restriction enzymes, probing with radioactively labelled fragments, or DNA sequencing, or any combination of these).

The resulting plasmid with the RB1B gC gene cloned into the HVT TK gene can then be introduced into the HVT genome by transfecting the plasmid into HVT-infected cells using calcium phosphate precipitation or electroporation. Homologous recombination, involving cross-overs either side of the gC gene, between the HVT virus and the flanking sequences of the HVT TK plasmid will carry the RB1B gC gene into the HVT viral genome. Viral recombinants can be selected for (as they are TK-) or identified (eg by probing) as described above.

In analogous ways, the sequence information given above and in the Figures can be used to design cloning strategies for the insertion of these genes and others into the non-essential genes of the ILTV described here or to generate combinations of antigen genes into ILTV.

What is claimed is:

1. A recombinant ILTV synthetically modified by the presence, in a non-essential region of the ILTV genome, of DNA not naturally occurring in ILTV.

2. The ILTV of claim 1 wherein the DNA is expressed in a host by the production of a protein.

3. An ILTV according to claim 1 wherein the DNA not naturally occurring in ILTV codes for an antigen or an antigenic part of the antigen, and comes from HVT, MDV, ILTV, IBV, IBDV, Newcastle Disease, Eimeria, avian encephalomyelitis, avian influenza, avian leukosis, avian paramyxoviruses, avian reovirus diseases, chicken anaemia, coccidiosis, egg drop syndrome, fowl pox, inclusion body hepatitis, lymphoproliferative disease of turkey, reticuloendotheliosis in chickens, reticuloendotheliosis in turkeys, rotavirus enteritis, turkey hemorrhagic enteritis or turkey rhinotrachemtis, or for paramyosin or an antigenic part thereof, somatostatin or a growth-promoting part thereof or an immune regulator.

4. The ILTV of claim 2 wherein the protein is an antigen.

5. An ILTV according to claim 3 wherein the DNA not naturally occurring in ILTV is selected from the group consisting of the nucleotide sequences shown in FIGS. 2A–2R, FIGS. 4A–4H, FIGS. 6A–6F, FIG. 11, FIG. 12, FIG. 13, FIG. 14, FIG. 15 and FIG. 16.

* * * * *